United States Patent
Torgov et al.

(10) Patent No.: US 12,319,707 B2
(45) Date of Patent: Jun. 3, 2025

(54) DOSAGE UNIT FORM(S) COMPRISING BTS AND BTS(OMe) FOR USE IN BORON NEUTRON CAPTURE THERAPY AND METHODS THEREOF

(71) Applicant: TAE Life Sciences, Irvine, CA (US)

(72) Inventors: Michael Y. Torgov, Redondo Beach, CA (US); Tioga J. Martin, Los Angeles, CA (US)

(73) Assignee: TAE Life Sciences, LLC, Irvine, CA (US)

( * ) Notice: Subject to any disclaimer, the term of this patent is extended or adjusted under 35 U.S.C. 154(b) by 0 days.

(21) Appl. No.: 18/445,603

(22) Filed: Nov. 15, 2023

(65) Prior Publication Data

US 2024/0092808 A1 Mar. 21, 2024

Related U.S. Application Data

(63) Continuation of application No. 17/803,487, filed on Aug. 1, 2022, now Pat. No. 11,884,688.

(60) Provisional application No. 63/259,662, filed on Jul. 30, 2021.

(51) Int. Cl.
*C07F 5/02* (2006.01)

(52) U.S. Cl.
CPC .................................... *C07F 5/025* (2013.01)

(58) Field of Classification Search
CPC .................................................... C07F 5/025
See application file for complete search history.

(56) References Cited

U.S. PATENT DOCUMENTS

| 8,765,997 B2 * | 7/2014 | Shaw | C07F 5/02 562/445 |
| 11,566,031 B2 * | 1/2023 | Torgov | A61K 41/0095 |
| 11,884,688 B2 * | 1/2024 | Torgov | A61P 35/00 |

* cited by examiner

*Primary Examiner* — Golam M Shameem
(74) *Attorney, Agent, or Firm* — LOSMP; Shane M. Popp

(57) ABSTRACT

Borylated Amino Acid compositions comprising tyrosine derivatives BTS and BTS(OMe) and novel methods of making BTS and BTS(OMe) are disclosed herein. Consequently, the BTS and/or BTS(OMe) can be scaled up to commercial scale and administered to patients as a Neutron Capture Agent and provide a method of treating cancer, immunological disorders, and other disease by utilizing a Neutron Capture Therapy modality.

11 Claims, 27 Drawing Sheets

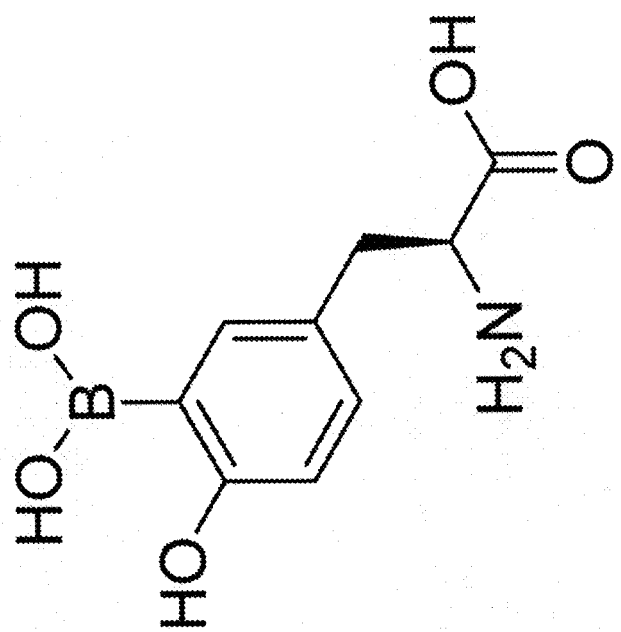
Figure 1. Chemical Structure of BTS

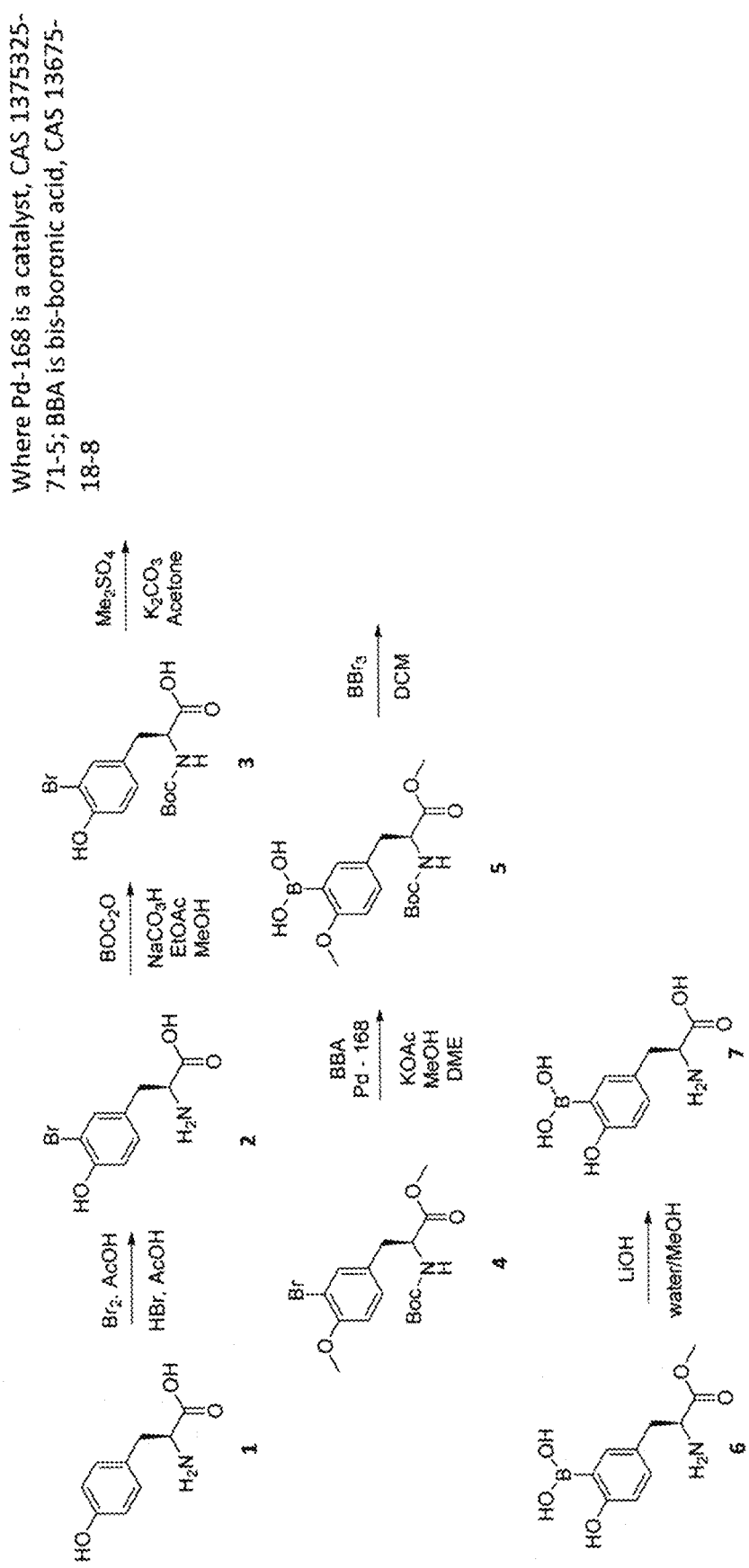
Figure 2. Chemical Synthesis for BTS
Where Pd-168 is a catalyst, CAS 1375325-71-5; BBA is bis-boronic acid, CAS 13675-18-8

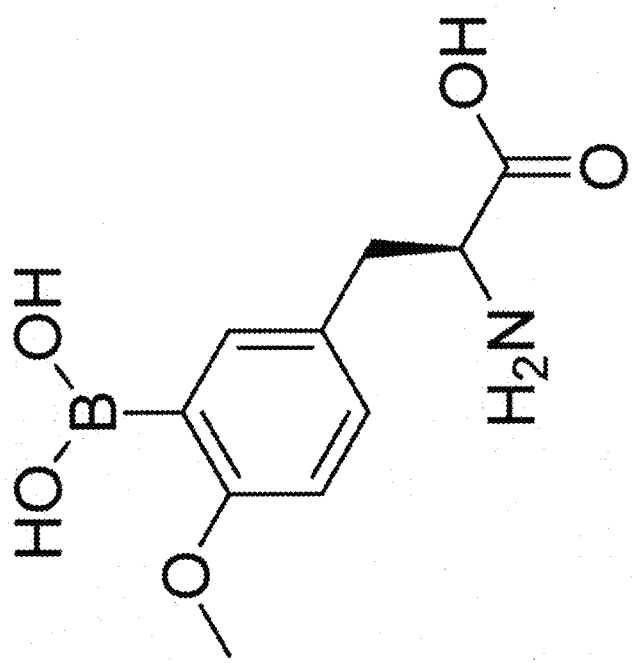
Figure 3. Chemical Structure of BTS(OMe)

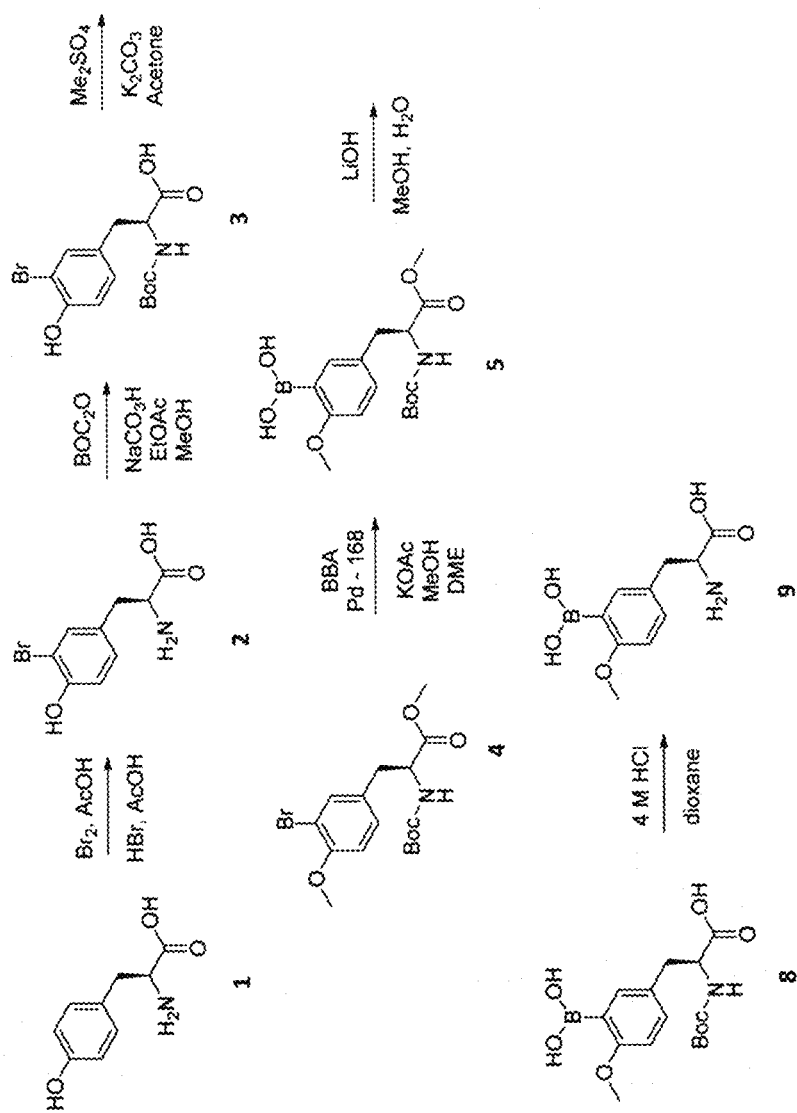
Figure 4. Chemical Synthesis for BTS(OMe)

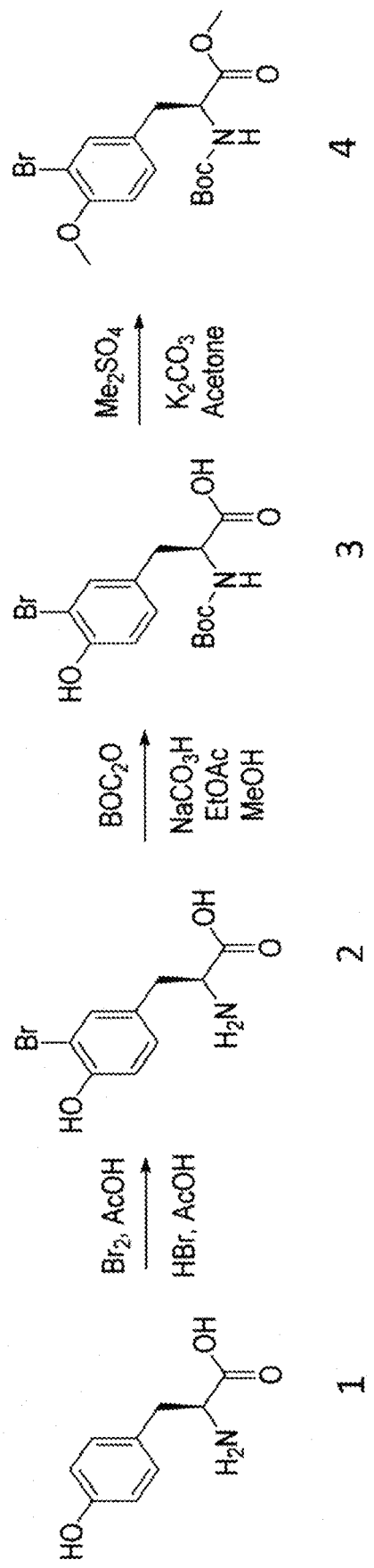
Figure 5. Chemical Synthesis for Tyr to Boc-Tyr(3-Br, 4-OMe)-OMe

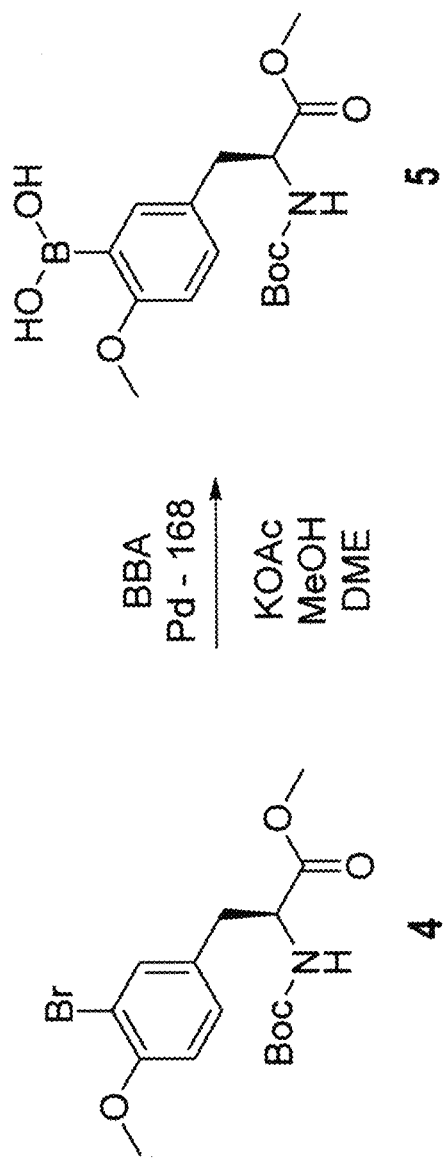
Figure 6. Chemical Synthesis for Tyr to Boc-Tyr(3-Br, 4-OMe)-Ome to Boc-Tyr(3-B(OH)₂, 4-OMe)-OMe

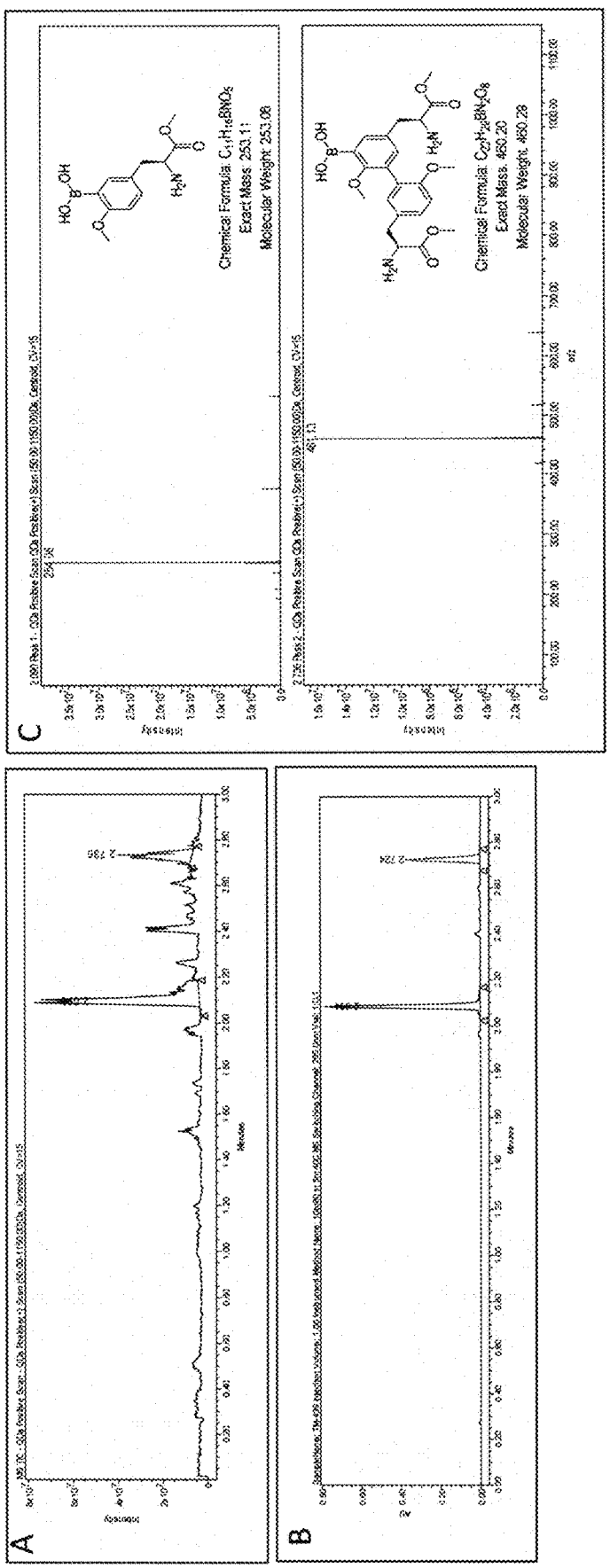
Figure 7. The Main Product and a By-Product of Pd Coupling Reaction

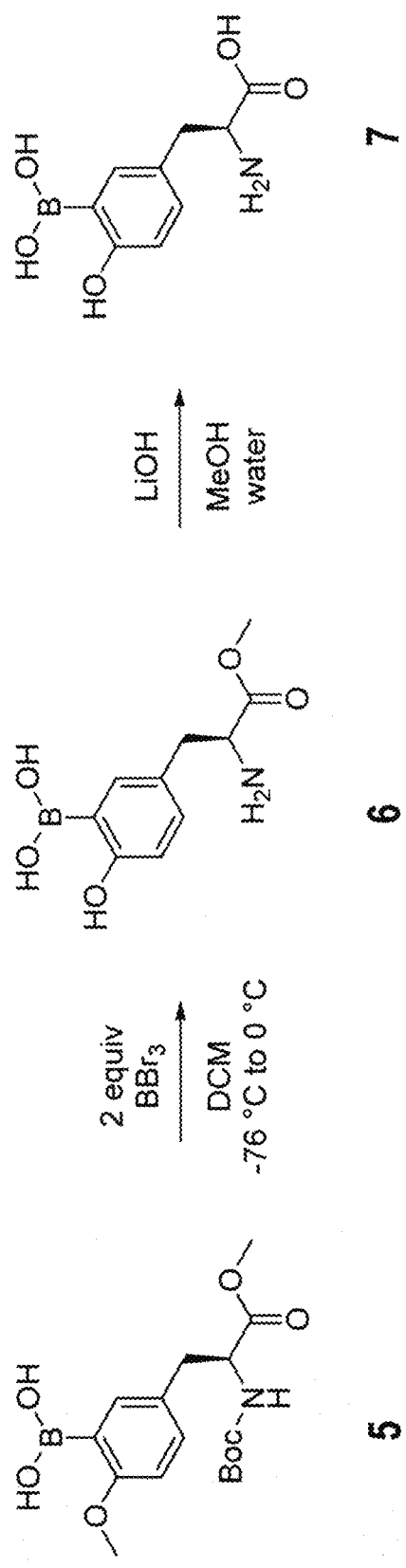
Figure 8. Chemical Synthesis of BTS from Boc-Tyr(3-B(OH)₂, 4-OMe)-OMe

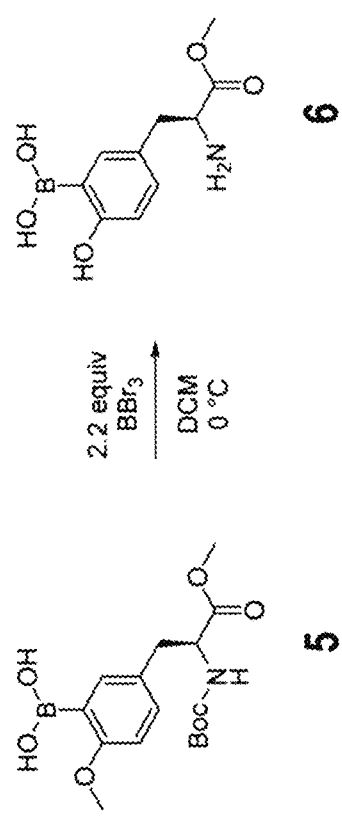
Figure 9. Chemical Synthesis for BTS-OMe from Boc-Tyr(3-B(OH)$_2$, 4-OMe)-OMe

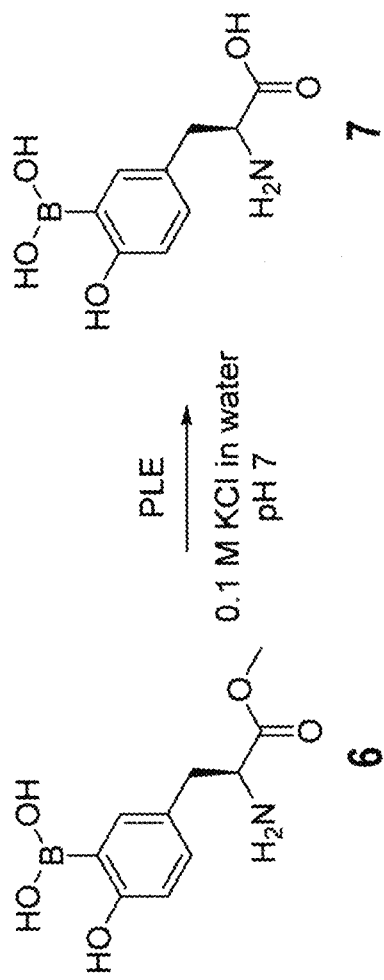
Figure 10. Chemical Synthesis for BTS from Tyr(3-B(OH)$_2$)-OMe Using Porcine Liver Esterase (PLE)
(A)

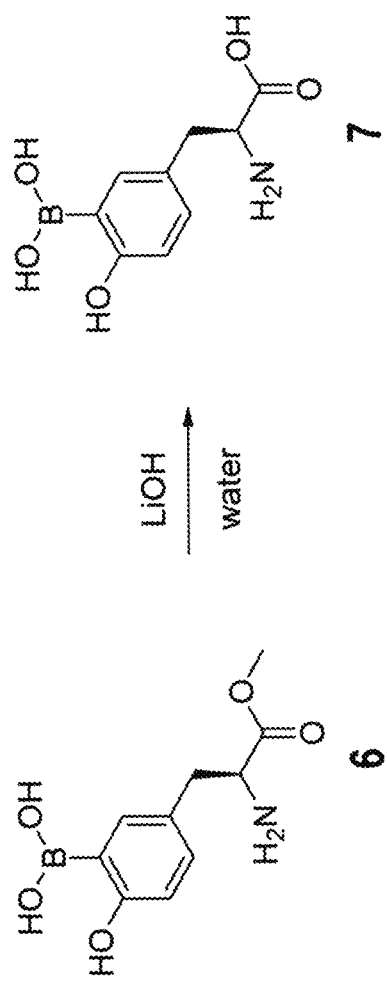
Figure 10, continued. Chemical Synthesis for BTS from Tyr(3-B(OH)$_2$)-OMe Using LiOH.

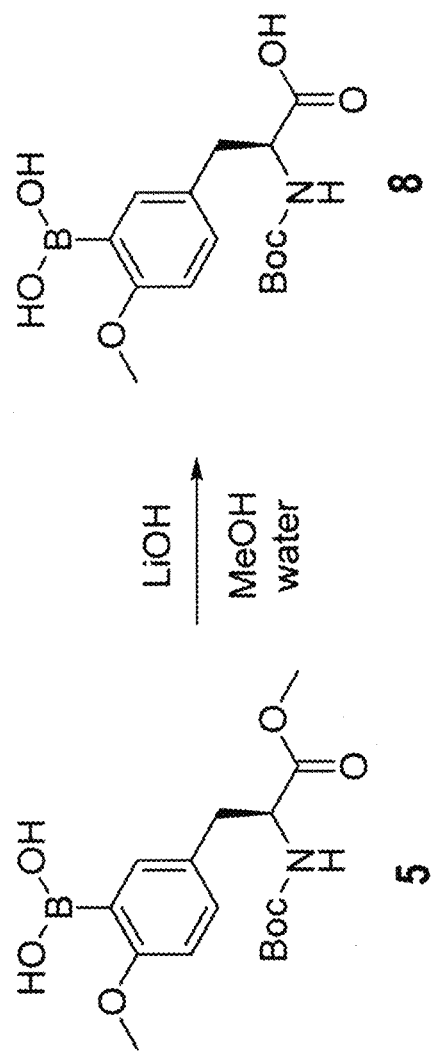
Figure 11. Chemical Synthesis for Boc-Tyr(3-B(OH)$_2$, 4-OMe)-OMe to Boc-Tyr(3-B(OH)$_2$, 4-OMe)-OH

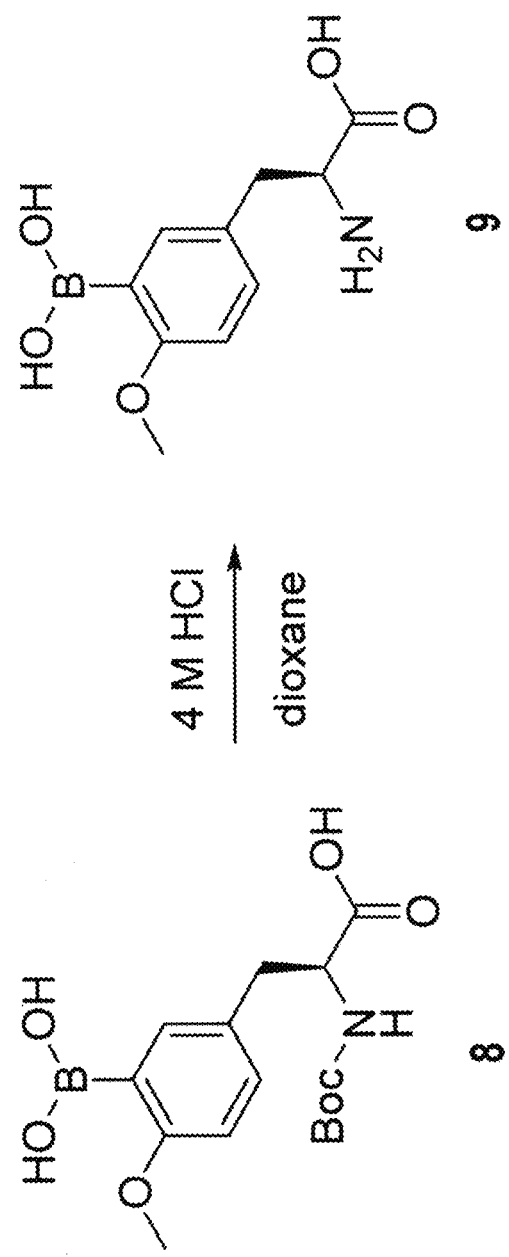
Figure 12. Chemical Synthesis for Boc-Tyr(3-B(OH)₂, 4-OMe)-OH to BTS(OMe)

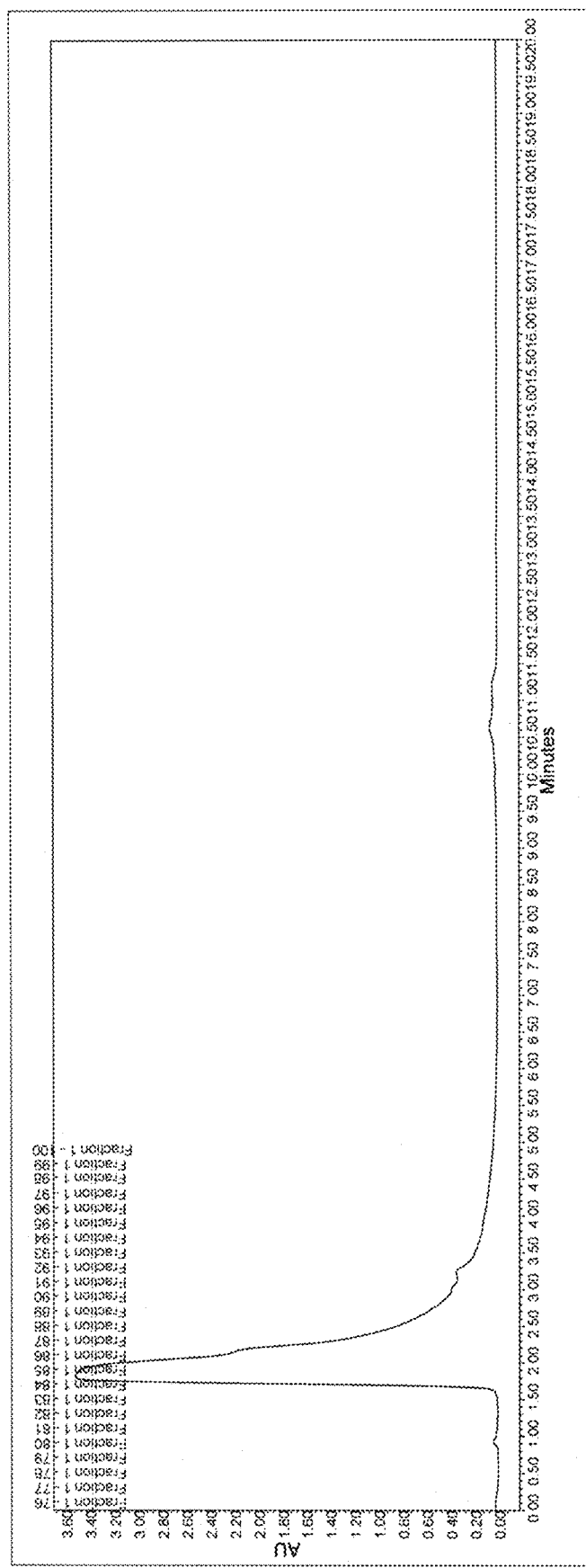
Figure 13. Preparative Purification of BTS and BTS(OMe).

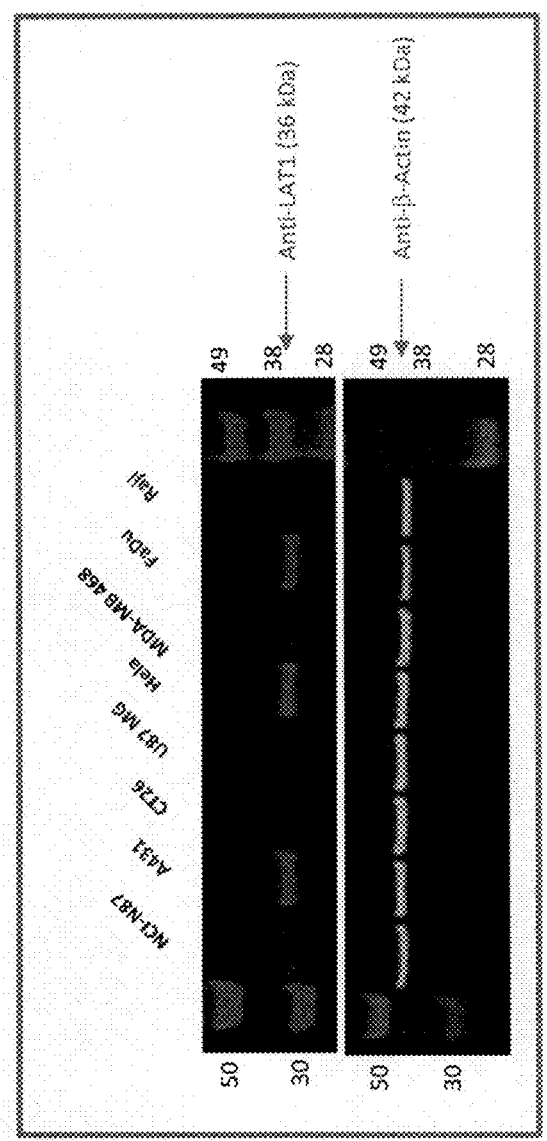
Figure 14. LAT1 Expression Analysis In A Panel of Cell Lines

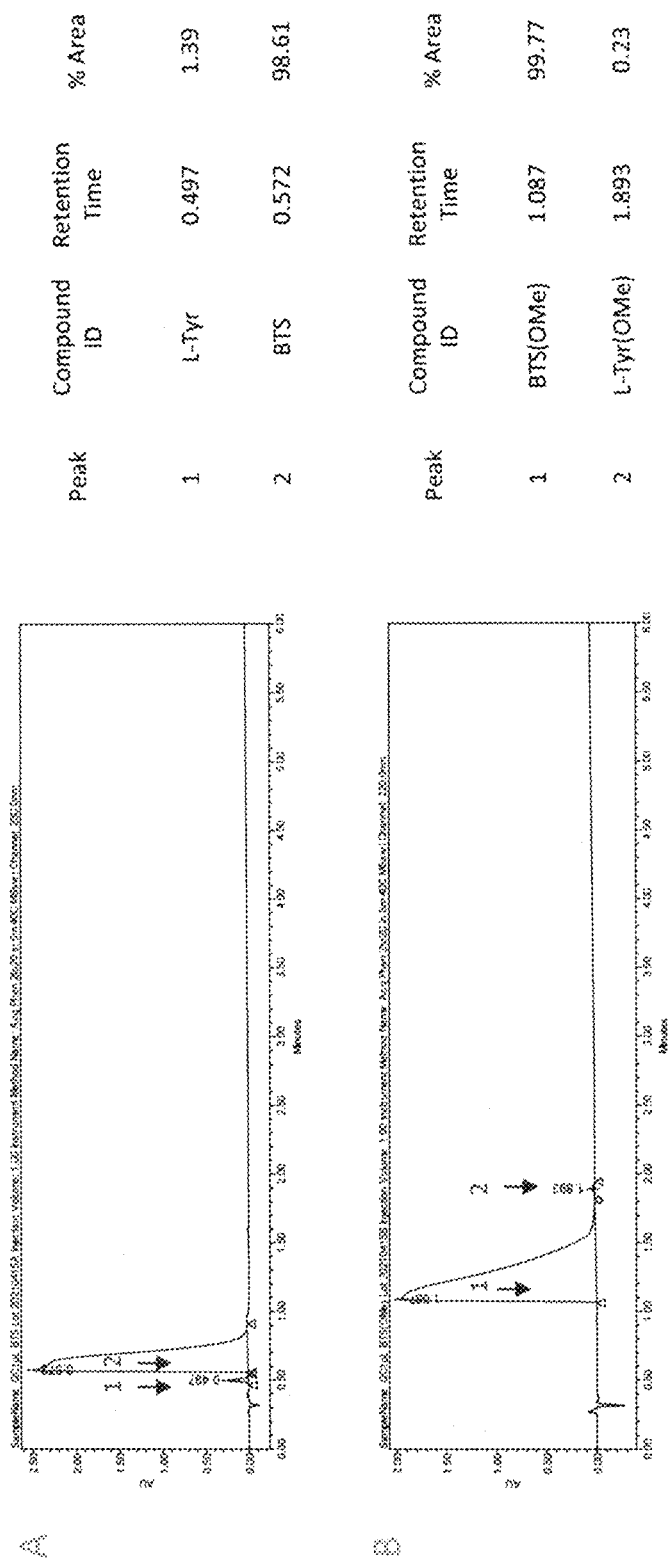
Figure 15. Analysis for Purity of BTS and BTS(OMe) Working Stock

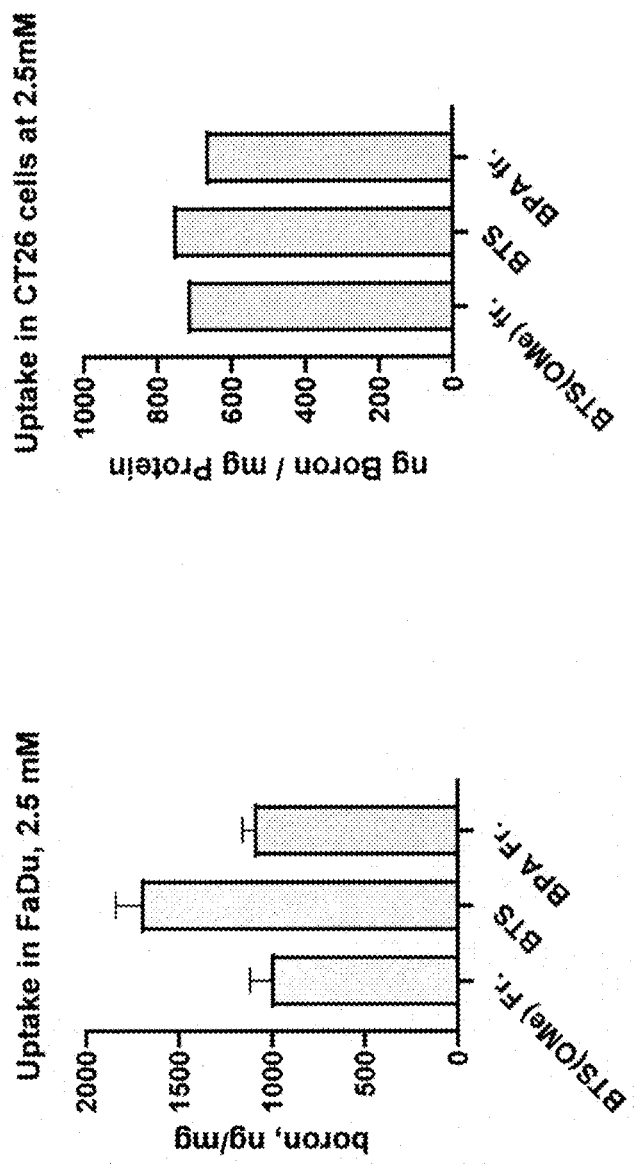
Figure 16. Compound Uptake in FaDu and CT26 Cells In Vitro

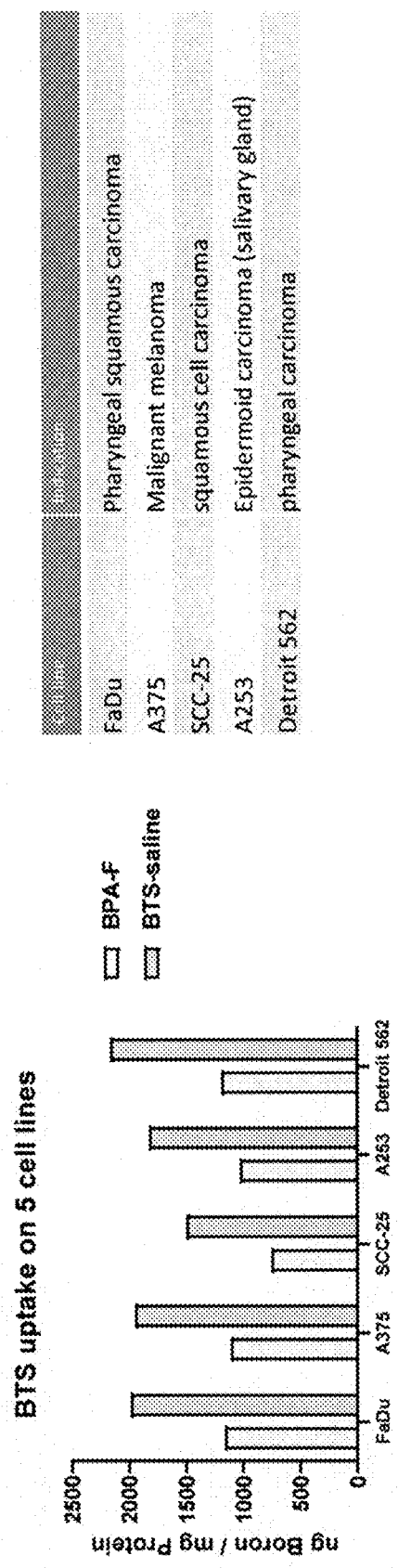
Figure 17. BTS Uptake Across Multiple Head and Neck Cancer Cell Lines

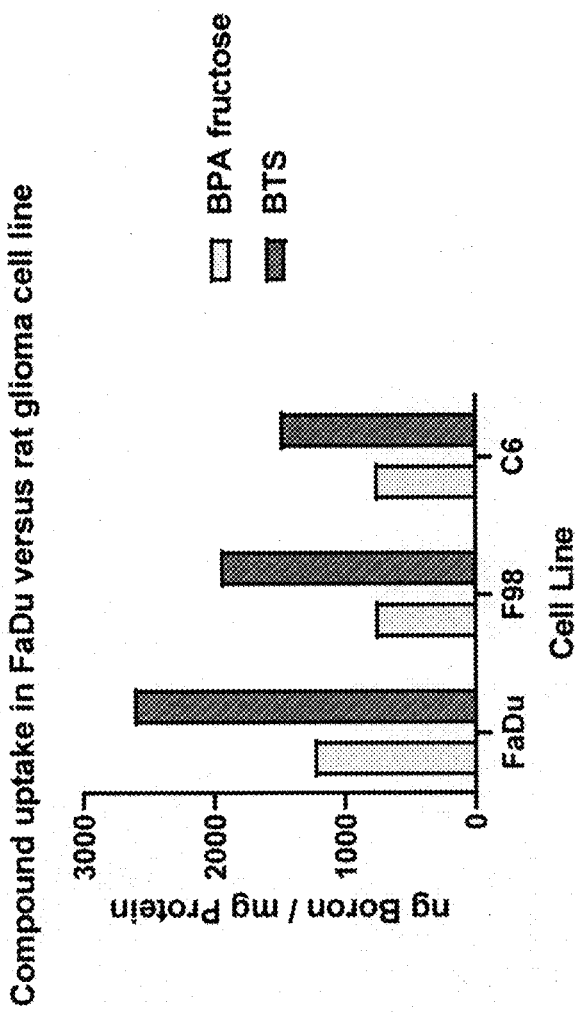
Figure 18. BTS Uptake Using Rat Glioma Cell Lines

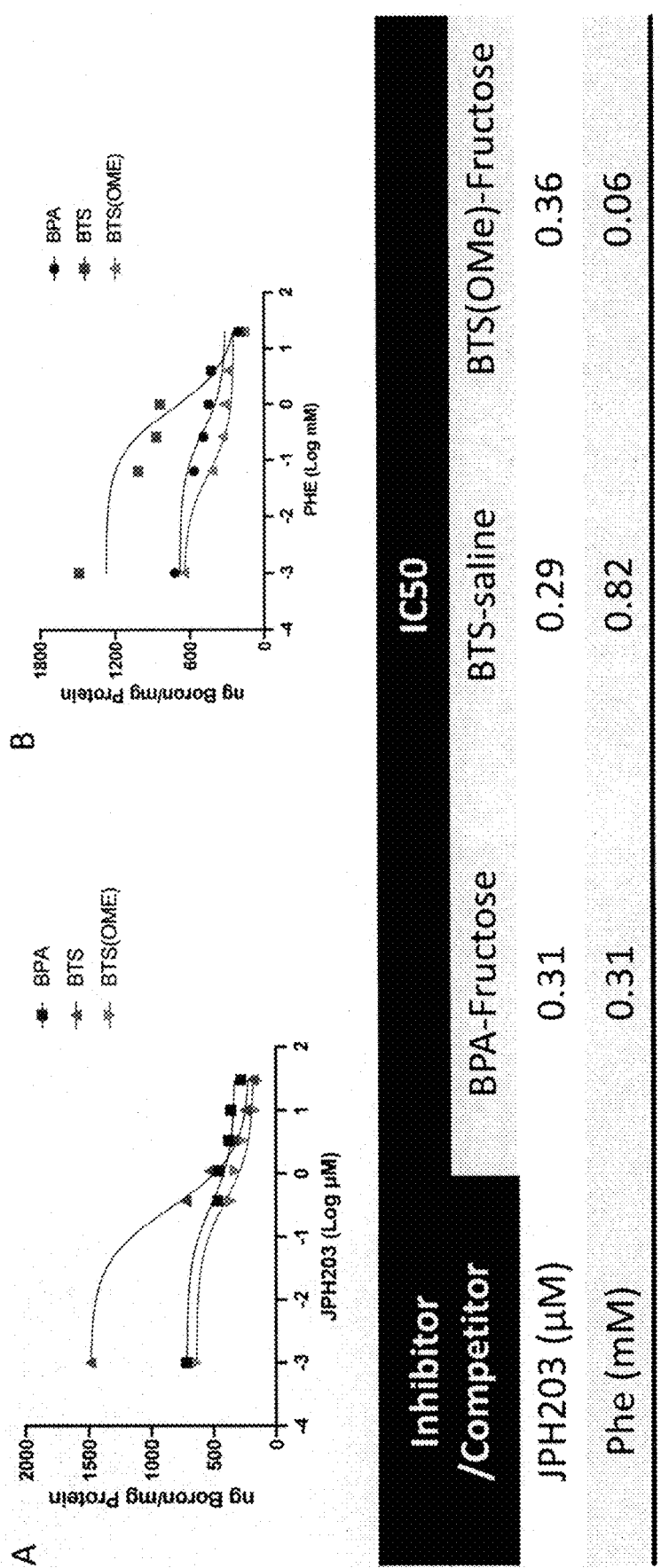
Figure 19. Uptake Competition Assay

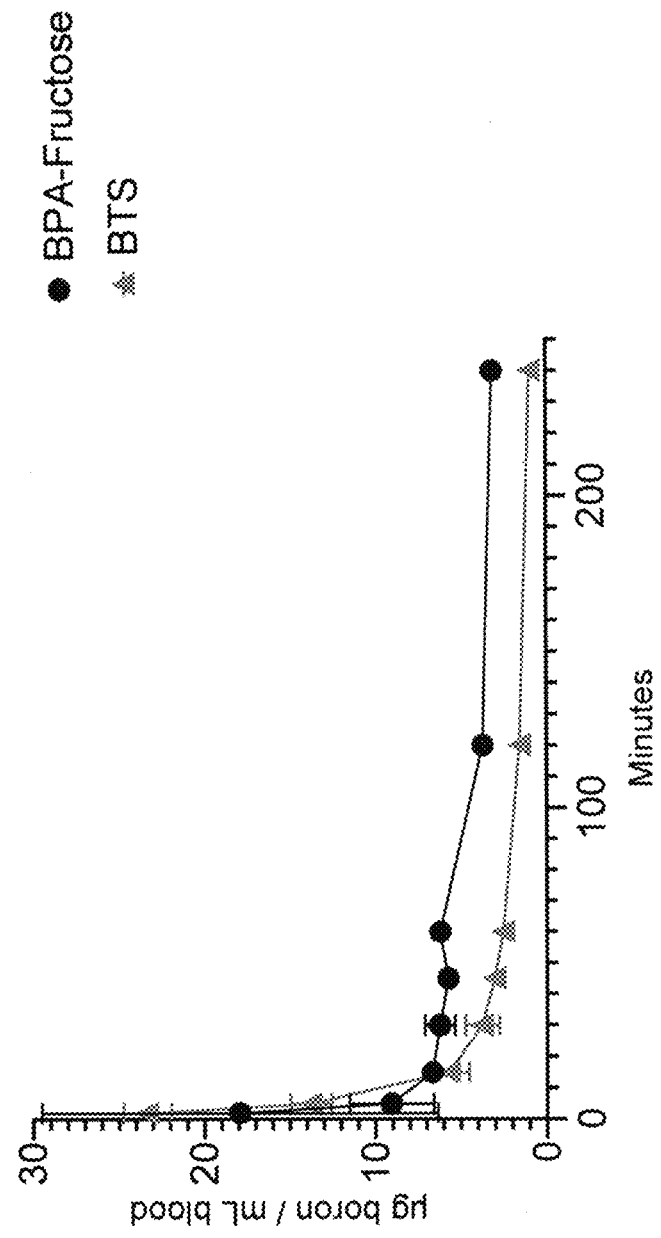
Figure 20. Pharmacokinetics in Non-Tumor-Bearing Mice

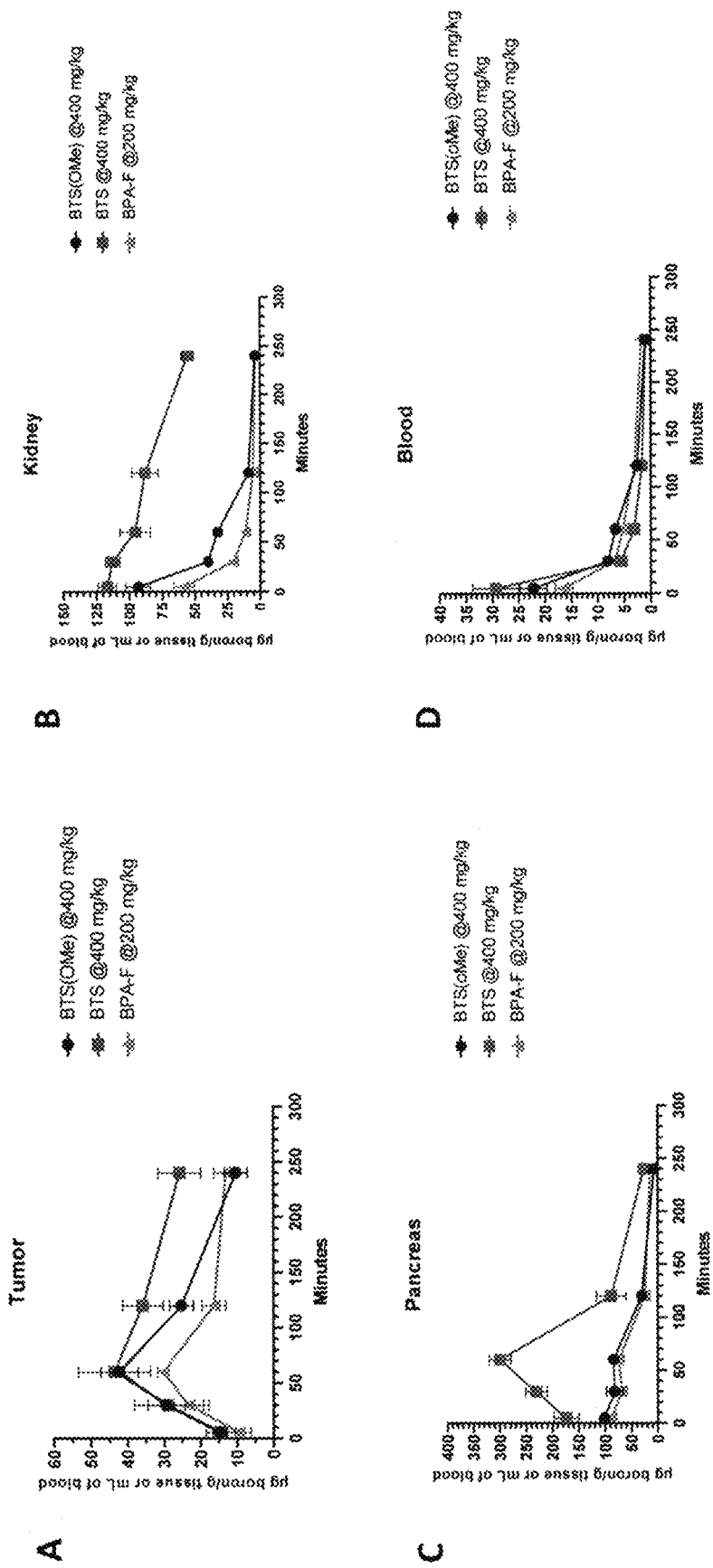

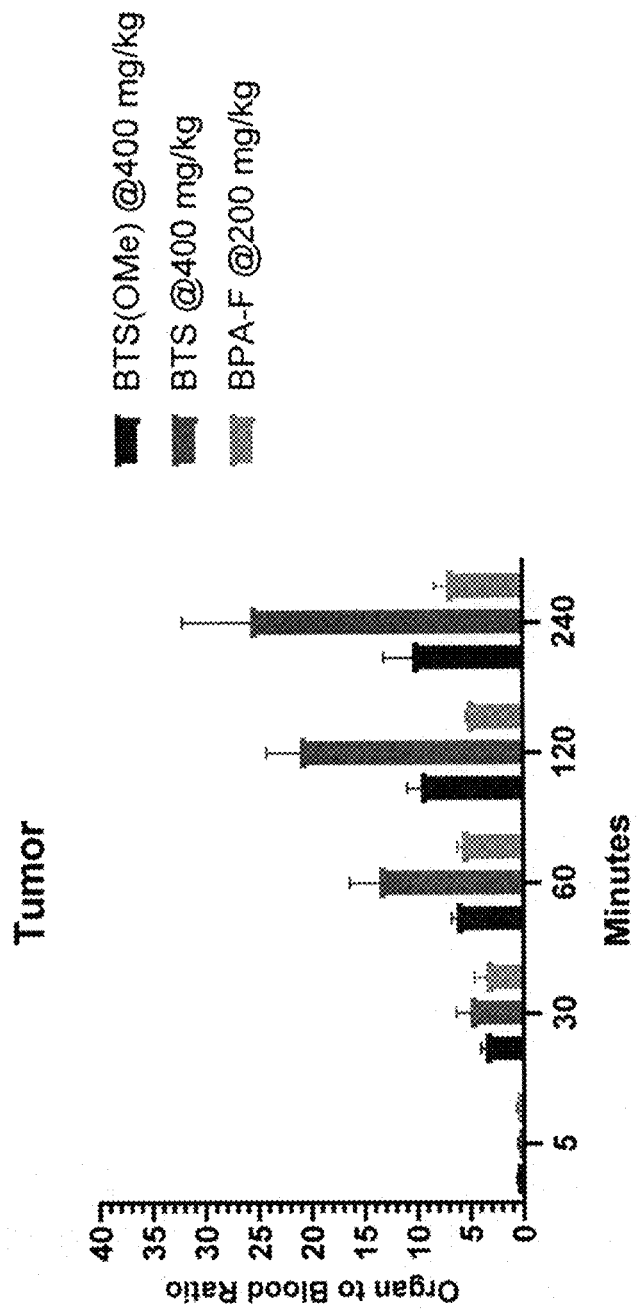
Figure 22. Tumor to Blood Ratio Using Subcutaneous Established FaDu Xenografts

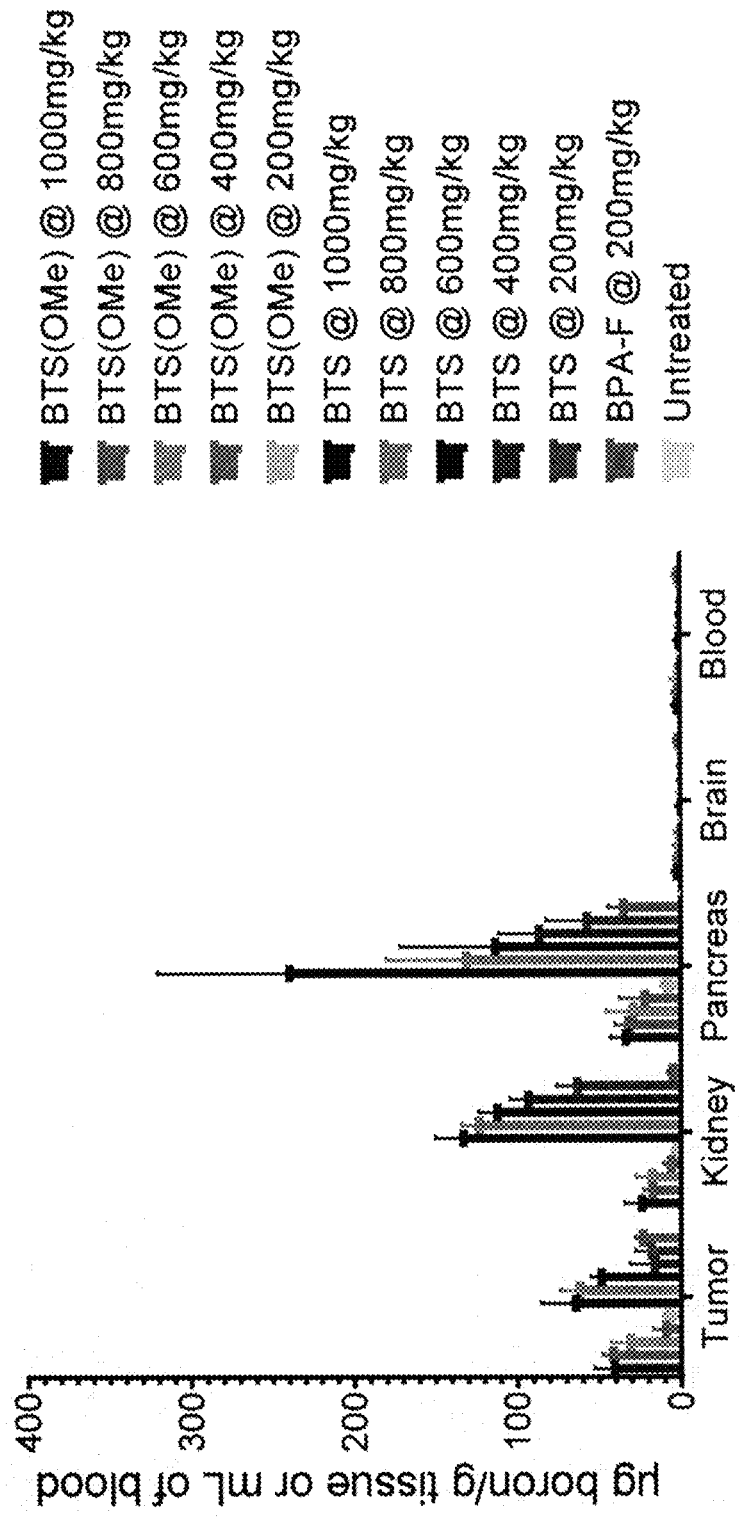
Figure 23. Dose Titration and Biodistribution Studies Using Subcutaneous FaDu Xenografts

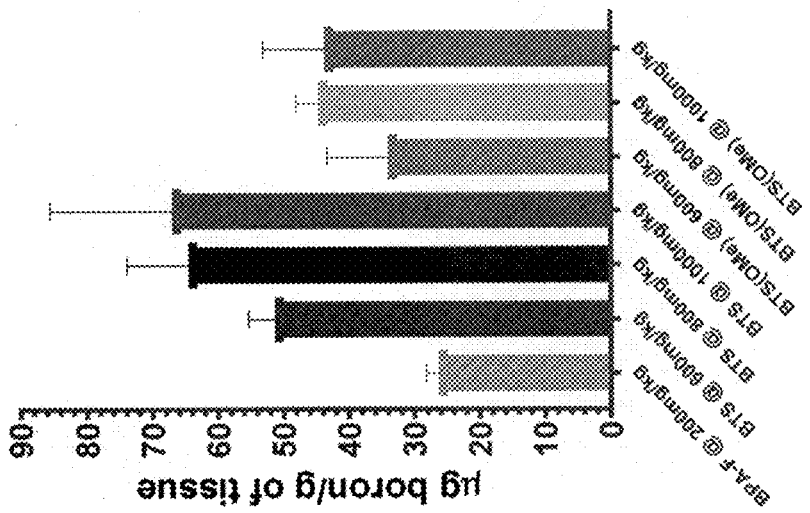
Figure 24. Dose Titration and Biodistribution Studies: Boron Uptake

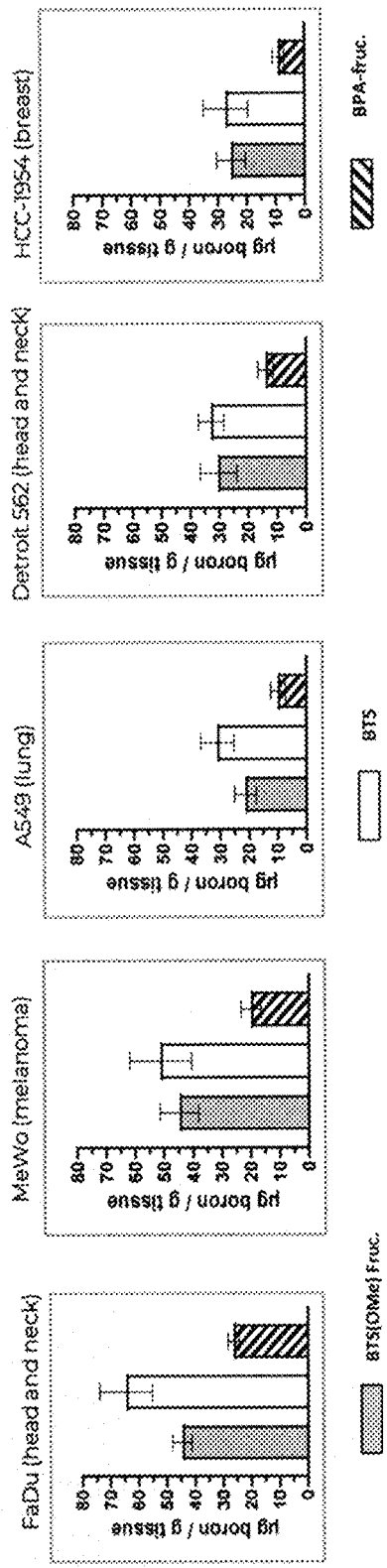
Figure 25. Boron Uptake Across Panel(s) of Established Tumor Xenografts

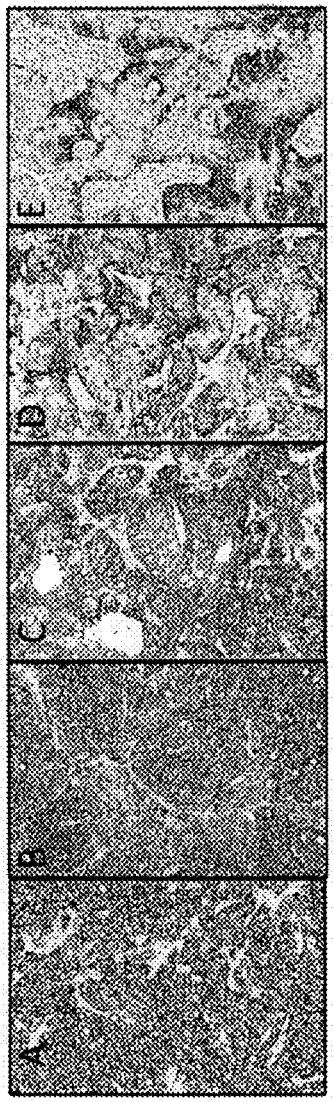
Figure 26. LAT1 Expression by IHC Across Established Tumor Xenografts

DOSAGE UNIT FORM(S) COMPRISING BTS AND BTS(OMe) FOR USE IN BORON NEUTRON CAPTURE THERAPY AND METHODS THEREOF

CROSS-REFERENCE TO RELATED APPLICATIONS

This application is a continuation of U.S. Ser. No. 17/803,487, filed 1 Aug. 2022, which claims priority to U.S. Provisional Patent Application No. 63/259,662 filed 30 Jul. 2021, the contents of which are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to the field of boron neutron capture therapy (BNCT). Specifically, the invention relates to borylated amino acid ("BAA") or ("BAAs") compositions, including BTS and BTS(OMe), which can be used as a vehicle for neutron capture therapy in humans. The invention further relates to the treatment of cancers and other immunological disorders and diseases.

BACKGROUND OF THE INVENTION

Cancer is the second leading cause of death next to coronary disease worldwide. Millions of people die from cancer every year and in the United States alone cancer kills well over a half-million people annually, with 1,688,780 new cancer cases diagnosed in 2017 (American Cancer Society). While deaths from heart disease have been declining significantly, those resulting from cancer generally are on the rise. In the early part of the next century, cancer is predicted to become the leading cause of death unless medical developments change the current trend.

Several cancers stand out as having high rates of mortality. In particular, carcinomas of the lung (18.4% of all cancer deaths), breast (6.6% of all cancer deaths), colorectal (9.2% of all cancer deaths), liver (8.2% of all cancer deaths), and stomach (8.2% of all cancer deaths) represent major causes of cancer death for both sexes in all ages worldwide (GLOBOCAN 2018). These and virtually all other carcinomas share a common lethal feature in that they metastasize to sites distant from the primary tumor and with very few exceptions, metastatic disease fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neck and lung adenocarcinoma) which are sometimes limited to standard radiotherapy and/or chemotherapy. Nonetheless, detrimental effects of these therapies are chemo- and radio resistance, which promote loco-regional recurrences, distant metastases and second primary tumors, in addition to severe side-effects that reduce the patients' quality of life.

Neutron Capture Therapy (NCT) is a promising form of radiation therapy. It is a technique that selectively kills tumor cells using boron compound while sparing the normal cells. BNCT relies on the propensity of non-radioactive $^{10}B$ isotope to absorb epithermal neutrons that fall into the low energy range of 0.5 keV$<E_n<$30 keV. Following neutron capture, boron atom undergoes a nuclear fission reaction giving rise to an alpha-particle and a recoiled lithium nucleus ($^1Li$) as follows:

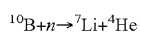

$$^{10}B+n\rightarrow{}^7Li+{}^4He$$

The alpha particle deposits high energy i.e., 150 keV/μm along their short path essentially restricted to a single cell diameter that results in a double strand DNA break followed by cancer cell death by apoptosis. Thus, BNCT integrates a concept of both chemotherapy, targeted therapy, and the gross anatomical localization of traditional radiotherapy.

Even though the conceptual techniques of NCT and specifically Boron Neutron Capture Therapy (BNCT) are well known, the technological limitations associated with this type of treatment have slowed progress. During the early investigations using the research reactors of MIT in 1960's, several dozens of patients were treated using disodium decahydrodecaborate, which was considered less toxic than simple boron compounds used previously yet capable of delivering more boron to the cell. Unfortunately, BNCT studies were halted in the USA due to the severe brain necrosis in the patients undergoing BNCT and the potential harm of using nuclear reactors.

Hiroshi Hatanaka in 1968 re-investigated clinical application of BNCT in Japan using sodium borocaptate (BSH) by directing the beam to surgically exposed intracranial tumor and reported of achieving 58% of 5-year survival rate. In 1987 clinicians in Japan applied BNCT for the treatment of malignant melanoma using boronophenylalanine (BPA) as boron compound. Thus, slow resurgence of BNCT took place albeit limited to the countries with an access to research reactor facilities capable of delivering epithermal neutron beam. Currently, given the technological improvements in both (i) the infusion and delivery of a capture compound, which preferably concentrates in the tumor, and (ii) more abundant and easier access to neutron beam using cyclotrons, there has been a resurgence in NCT treatment methods.

The proton boron fusion reaction relies on the naturally abundant $^{11}B$ isotope rather than $^{10}B$ required for BNCT. Unlike BNCT, three alpha particles are emitted after the fusion reaction between a proton ($^1H$) and a boron ($^{11}B$) nucleus: $p+{}^{11}B\rightarrow 3\alpha$. The proton beam has the advantage of a Bragg-peak characteristic reducing the normal tissue damage and when combined with proton capture, may improve the efficacy of the proton therapy alone.

Carriers of boron have evolved since 1950s and are reviewed in NEDUNCHEZHIAN, et. al., J. Clin. Diag. Res., vol. 10(12) (December 2016). Briefly, the $1^{st}$ generations of boron compounds represented by boric acid and its derivatives were either toxic or suffered from low tumor accumulation/retention. BPA and BSH are both considered the $2^{nd}$ generation compounds that emerged in 1960s. These had significantly lower toxicity and better PK and biodistribution. BPA-fructose complex is considered the $3^{rd}$ generation compound that is used to treat patients with H&N, glioblastoma and melanoma using BNCT since 1994. BPA-fructose and BSH are the only compounds that are being used in clinic as boron carriers to date although both low and high molecular weight biomolecules such as nucleosides, porphyrins, liposomes, nanoparticles and mAbs have been evaluated for the tumor targeting in preclinical models. The main deficiency of BPA-fructose is relatively low solubility combined with its rapid clearance that prevents achieving high Cmax in blood, one of the drivers influencing the tumor uptake.

From the aforementioned, it will be readily apparent to those skilled in the art that a new treatment paradigm is needed, in the treatment of cancers and immunological diseases. By using modern chemical synthesis and modifying natural amino acids with boron, a new disease treatment can be achieved with the overall goal of more effective treatment, reduced side effects, and lower production costs.

Given the current deficiencies associated with NCT, it is an object of the present invention to provide new and improved methods of treating cancer(s), immunological disorders, and other diseases utilizing borylated amino acids and NCT.

SUMMARY OF THE INVENTION

The invention provides for compositions comprising natural amino acids which have been borylated via chemical synthesis for use as a delivery modality to treat human diseases such as cancer, immunological disorders, including but not limited to rheumatoid arthritis, ankylosing spondylitis, and other cellular diseases, including but not limited to Alzheimer's disease. In certain embodiments, the borylated amino acids are comprised of naturally occurring amino acids such as phenylalanine, tryptophan, tyrosine, histidine, and any other naturally occurring amino acid set forth in Table I.

In a further embodiment, the invention comprises BTS.

In a further embodiment, the invention comprises BTS(OMe).

In a further embodiment, the invention comprises methods of synthesizing BTS.

In a further embodiment, the invention comprises methods of synthesizing BTS(OMe).

In a further embodiment, the invention comprises methods of concentrating Boron in a cell comprising (i) synthesizing a borylated amino acid ("BAA"); (ii) administering the BAA to a patient, and (iii) irradiating the cell with neutrons.

In a further embodiment, the invention comprises methods of concentrating Boron in a cell comprising (i) synthesizing BTS (ii) administering the BTS to a patient, and (iii) irradiating the cell with neutrons.

In a further embodiment, the invention comprises methods of concentrating Boron in a cell comprising (i) synthesizing BTS(OMe) (ii) administering the BTS(OMe) to a patient, and (iii) irradiating the cell with neutrons.

In another embodiment, the present disclosure teaches methods of synthesizing BAA's.

In another embodiment, the present disclosure teaches methods of treating cancer(s), immunological disorders, and other diseases in humans.

BRIEF DESCRIPTION OF THE FIGURES

FIG. 1. Chemical Structure of BTS.
FIG. 2. Chemical Synthesis for BTS.
FIG. 3. Chemical Structure of BTS(OMe).
FIG. 4. Chemical Synthesis for BTS(OMe).
FIG. 5. Chemical Synthesis for Tyr to N-Boc-Tyr(3-Br, 4-OMe)-OMe.
FIG. 6. Chemical Synthesis for Tyr to N-Boc-Tyr(3-Br, 4-OMe)-OMe to N-Boc-Tyr(3-B(OH)$_2$, 4-OMe)-OMe.
FIG. 7. The Main Product and a By-Product of Pd Coupling Reaction.
FIG. 8. Chemical Synthesis of BTS from N-Boc-Tyr(3-B(OH)$_2$, 4-OMe)-OMe.
FIG. 9. Chemical synthesis of BTS-OMe from N-Boc-Tyr(3-B(OH)$_2$, 4-OMe)-OMe.
FIG. 10. (A). Chemical Synthesis for BTS from Tyr(3-B(OH)$_2$)—OMe using Porcine Liver Esterase (PLE). (B). Chemical Synthesis for BTS from Tyr(3-B(OH)$_2$)—OMe using LiOH.
FIG. 11. Chemical Synthesis for N-Boc-Tyr(3-B(OH)$_2$, 4-OMe)-OMe to Boc-Tyr(3-B(OH)$_2$, 4-OMe)-OH.
FIG. 12. Chemical Synthesis for N-Boc-Tyr(3-B(OH)$_2$, 4-OMe)-OH to BTS(OMe).
FIG. 13. Preparative HPLC Purification of BTS and BTS(OMe).
FIG. 14. LAT1 Expression Analysis in a panel of cell lines.
FIG. 15. Analysis for Purity of BTS and BTS(OMe) Working Stock.
FIG. 16. Compound Uptake in FaDu and CT26 Cells In Vitro.
FIG. 17. BTS Uptake Across Multiple Head and Neck Cancer Cell Lines.
FIG. 18. BTS Uptake Using Rat Glioma Cell Lines.
FIG. 19. Uptake Competition Assay.
FIG. 20. Pharmacokinetics in Non-Tumor-Bearing Mice.
FIG. 21. BTS and BTS(OMe) Time-Course in Mice Bearing Subcutaneous FaDu Tumors.
FIG. 22. Tumor to Blood Ratio Using Subcutaneous Established FaDu Xenografts.
FIG. 23. Dose Titration and Biodistribution Studies Using Subcutaneous FaDu Xenografts.
FIG. 24. Dose Titration and Biodistribution Studies: Boron Uptake.
FIG. 25. Boron Uptake Across Panel(s) of Established Tumor Xenografts.
FIG. 26. LAT1 Expression by IHC Across Established Tumor Xenografts.

DETAILED DESCRIPTION OF THE INVENTION

Outline of Sections
  I.) Definitions
  II.) BPA
  III.) BSH
  IV.) Boron
    a. Boron Generally
  V.) Naturally Occurring Amino Acids
  VI.) Borylated Amino Acids (BAAs)
    a. Amino Acid Compositions
    b. BAA Comprising Tyrosine (BTS and BTS(OMe)
    c. New and Improved Synthesis of BTS and BTS (OMe)
  VII.) Boron Neutron Capture Therapy Using BTS & BTS(OMe)
  VIII.) Proton Boron Fusion Therapy Using BTS & BTS (OMe)
  IX.) Methods of Delivering BTS & BTS(OMe) to a Cell
  X.) KITS/Articles of Manufacture

I.) Definitions

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease and these patients have substantially less favorable outcomes compared to patients having clinically localized (organ-confined) cancer.

"Amino Acid" means a simple organic compound containing both a carboxyl (—COOH) and an amino (—NH$_2$) group.

"Borylation" means reactions that produce an organoboron compound through functionalization of aliphatic and aromatic C—H bonds.

"Borylated Amino Acid" (BAA) means a compound comprising a naturally occurring amino acid, such as those set forth in Table I, which has undergone a borylation reaction. BAAs can be synthesized in multiple formats depending on the underlying amino acid that is being used.

"BTS" means a compound comprising the chemical structure set forth in FIG. 1.

"BTS(OMe)" means a compound comprising the chemical structure set forth in FIG. 3.

The term "compound" refers to and encompasses the chemical compound (e.g. a BAA) itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above The terms "inhibit" or "inhibition of" as used herein means to reduce by a measurable amount, or to prevent entirely.

The term "mammal" refers to any organism classified as a mammal, including mice, rats, rabbits, dogs, cats, cows, horses, and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites and are meant to include stage D disease under the AUA system and stage T×N×M+ under the TNM system.

"Molecular recognition" means a chemical event in which a host molecule is able to form a complex with a second molecule (i.e., the guest). This process occurs through non-covalent chemical bonds, including but not limited to, hydrogen bonding, hydrophobic interactions, and ionic interaction.

"Pharmaceutically acceptable" refers to a non-toxic, inert, and/or composition that is physiologically compatible with humans or other mammals.

The term "neutron capture agent" means a stable non-reactive chemical isotope which, when activated by neutrons produces alpha particles.

The term "neutron capture therapy" means a noninvasive therapeutic modality for treating locally invasive malignant tumors such as primary brain tumors and recurrent head and neck cancer and other immunological disorders and disease by irradiating a neutron capture agent with neutrons.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

II.) BPA

By way of reference and for context of the prior art, ($^{10}$B)-BPA, L-BPA, or 4-Borono-L-phenylalanine (Sigma Aldrich, St. Louis, MO) is a synthetic compound with the chemical formula $C_9H_{12}BNO_4$. The structure is shown below:

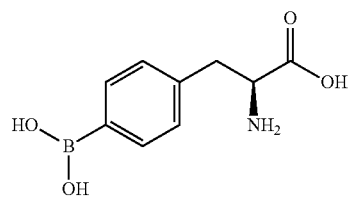 [SMILES: N[C@@H](Cc1ccc(B(O)O)cc1)C(=O)O]

and is an important boronated compound useful in the treatment of cancer though BNCT. It is a widely known compound which many syntheses have been developed (See, U.S. Pat. No. 8,765,997, Taiwan Biotech Co, Ltd., Taoyuan Hsein, Taiwan, and US2017/0015684, Stella Pharma Corp., Osaka Prefecture Univ., Osaka, Japan).

III.) BSH

In addition to BPA, BSH, or sodium borocaptate, or BSH sodium borocaptate, or Borocaptate sodium $^{10}$B, or undecahydro-closo-dodecaboratethiol is a known synthetic chemical compound with the chemical formula Na2B12H11SH. The structure is shown below:

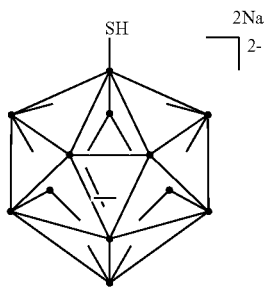

where boron atoms are represented by dots in the vertices for the icosahedron. BSH is used as a capture agent in BNCT. Generally speaking, BSH is injected into a vein and becomes concentrated in tumor cells. The patient then receives radiation treatment with atomic particles called neutrons. The neutrons fuse with the boron nuclei in BSH and to produce high energy alpha particles that kill the tumor cells.

IV.) Boron (a.) Boron Generally

Generally speaking, and for purposes of this disclosure, Boron is a chemical element with symbol B and atomic number 5. Primarily used in chemical compounds, natural boron is composed of two stable isotopes, once of which is Boron-10 and the other is Boron-11. Boron-10 isotope is useful for capturing epithermal neutrons, which makes it a promising tool in a therapeutic context using Boron Neutron Capture Therapy. Biologically, the borylated compounds disclosed herein are nontoxic to humans and animals. Based on the foregoing, it will be readily apparent to one of skill in the art that improved modalities for providing high concentrations of boron into a cancer cell are advantageous. It is an object of the present disclosure to provide that advantage.

V.) Naturally Occurring Amino Acids

Generally speaking, and for the purposes of this disclosure, naturally occurring amino acids are organic compounds containing amine (—NH$_2$) and carboxyl (—COOH) functional groups, along with a side chain (R group) specific to each amino acid. The key elements of an amino acid are carbon (C), hydrogen (H), oxygen (O), and nitrogen (N), although other elements are found in the side chains of certain amino acids. About 500 naturally occurring amino acids are known (though only 20 appear in the genetic code (Table I)) and can be classified in many ways. They can be classified according to the core structural functional groups' locations as alpha- (α-), beta- (β-), gamma- (γ-) or delta- (δ-) amino acids; other categories relate to polarity, pH level, and side chain group type (aliphatic, acyclic, aromatic, containing hydroxyl or sulfur, etc.). In the form of proteins, amino acid residues form the second-largest component (water is the largest) of human muscles and other tissues. Beyond their role as residues in proteins, amino acids participate in a number of processes such as neurotransmitter transport and biosynthesis.

The twenty (20) amino acids encoded directly by the genetic code (See, Table I) can be divided into several groups based on their properties. Principal factors are charge, hydrophilicity or hydrophobicity, size, and functional groups. These properties are important for protein structure and protein-protein interactions. The water-soluble proteins tend to have their hydrophobic residues (Leu, Ile, Val, Phe, and Trp) buried in the middle of the protein, whereas hydrophilic side chains are exposed to the aqueous solvent.

The integral membrane proteins tend to have outer rings of exposed hydrophobic amino acids that anchor them into the lipid bilayer. In the case part-way between these two extremes, some peripheral membrane proteins have a patch of hydrophobic amino acids on their surface that locks onto the membrane. In similar fashion, proteins that have to bind to positively charged molecules have surfaces rich with negatively charged amino acids like glutamate and aspartate, while proteins binding to negatively charged molecules have surfaces rich with positively charged chains like lysine and arginine. There are different hydrophobicity scales of amino acid residues.

Some amino acids have special properties such as cysteine, which can form covalent disulfide bonds to other cysteine residues, proline that forms a cycle to the polypeptide backbone, and glycine that is more flexible than other amino acids.

VI.) Borylated Amino Acids (BAAs)

By way of brief introduction and to better understand the background to the inventive endeavor of the present disclosure, it is noted that the large neutral amino acid transporter 1 (LAT-1, SLC7a5) is a sodium- and pH-independent transporter, which supplies essential amino acids (e.g., leucine, phenylalanine) to cells. The functional transporter is a heterodimeric disulfide-linked complex composed of the multi-transmembrane subunit SLC7a5 and single transmembrane subunit SLC3a2 (CD98). LAT-1 is the main transporter to channel essential amino acids across such compartments such as the placenta or blood-brain barrier. In addition, LAT-1 also transports the thyroid hormones T3 and T4 (See, FRIESEMA, et al., Endocrinology, 142(10): 4339-4348 (2001)), the dopamine precursor L-DOPA, as well as amino acid-related exogenous compounds, such as the drugs melphalan and gabapentin (See, UCHINO, et al., Mol. Pharmacol 61:729-737 (2002)). Moreover, its expression is highly upregulated in several types of human cancer that are characterized by an intense demand for amino acids for metabolism and growth (See, SINGH, et. al., Int. J. Mol. Sci. 2018, 19, 1278). Furthermore, it has been reported that the nature of the amino acid side chain influences selectivity of LAT-1 for various amino acids, with the following order in terms of increasing rate of transport: Phe>Trp>Leu>Ile>Met>His>Tyr>Val (See, KANAI, et al., J. Biol. Chem., vol. 273, No. 37, pp. 23629-23632 (1998)). However, the influence of additional boron modifications to amino acids is unknown in the art and this disclosure represents a pioneering breakthrough.

The therapeutic potential of BNCT as an effective cancer treatment rests in the selective accumulation of a sufficient amount of $^{10}B$ within cancer cells.

Based on the foregoing, those of ordinary skill in the art have shown that essential amino acid transporter proteins such as LAT1 are responsible for the uptake of certain naturally occurring amino acids. See, SCALISE, et. al., Frontiers in Chem., Vol. 6, Art. 243 (June 2018). With this principle in mind, the present disclosure contemplates the synthesis of naturally occurring amino acids through borylation reactions to create Borylated Amino Acids ("BAAs") with tumor seeking and tumor localizing properties for use as neutron capture agent in Boron Neutron Capture Therapy ("BNCT") and/or Boron Proton Capture Therapy commonly known as Proton Boron Fusion Therapy ("PBFT"). See, for example, HATTORI, et. al., J. Med. Chem., 55, 6980-6984 (2012).

(a) Amino Acid Composition(s)

In a further embodiment, a BAA with the following formula is within the scope of the of the present disclosure ("Tyrosine derivatives"):

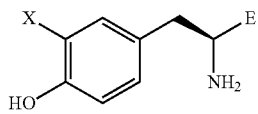

Where:
E=$CO_2H$, $CONHB_{12}H_{11}$, $B(OH)_2$; and
X=H, $B(OH)_2$, Bpin, ($-O-CH_2CH_2)_2-O-B_{12}H_{11}$ or $BF_3^-$.

In a further embodiment, a Tyrosine derivative with the following formula is within the scope of the of the present disclosure:

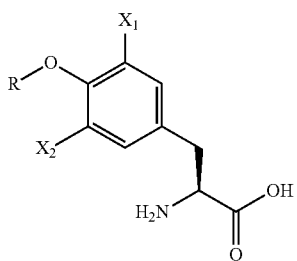

Where:
R=H, $CH_3$, or $CF_3$;
$X_1$=H, $B(OH)_2$, or $BF_3^-$; and
$X_2$=H, $B(OH)_2$, or $BF_3^-$ (a) BAA Comprising Tyrosine (BTS & BTS (OMe))

Tyrosine is an essential amino acid with the following chemical formula:

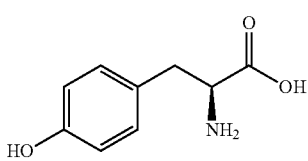 [SMILES: N[C@@H](Cc1ccc(O)cc1)C(=O)O]

and is known to readily pass the blood-brain barrier. Once in the brain, it is a precursor for the neurotransmitter's dopamine, norepinephrine, and epinephrine, better known as adrenalin. These neurotransmitters are an important part of the body's sympathetic nervous system, and their concentrations in the body and brain are directly dependent upon dietary tyrosine. Tyrosine is rapidly metabolized. Folic acid, copper, and vitamin C are cofactor nutrients of these reactions. Tyrosine is also the precursor for hormones, thyroid, catechol estrogens and the major human pigment, melanin. Tyrosine is an important amino acid in many proteins, peptides and even enkephalins, the body's natural pain reliever. Valine and other branched amino acids, and possibly tryptophan and phenylalanine may reduce tyrosine absorption. A number of genetic errors of tyrosine metabolism occur, such as Hawkins Nuria and tyrosinemia I. Most common is the increased amount of tyrosine in the blood of premature infants, which is marked by decreased motor activity, lethargy, and poor feeding. Infection and intellectual deficits may occur. Some adults also develop elevated tyrosine in their blood. This indicates a need for more vitamin C. Generally speaking, tyrosine is needed under stress, and tyrosine supplements prevent the stress-induced depletion of norepinephrine and may cure biochemical depression.

Additionally, various derivatives of tyrosine have been evaluated as tracers for whole-body imaging using PET and some are approved for specific indications, including neuroendocrine disorders and cancer. These include $^{18}F$-Fluoro-L-DOPA (DOI: 10.2967/jnumed.114.145730), $^{18}F$-Fluoro-L-alpha-methyltyrosine i.e., FAMT (INOUE, J Nucl. Med. 1998; 39:663-667 and 10.2967/jnumed.112.103069).

Furthermore, ISHIWATA, et. al. described O-[$^{18}F$]fluoromethyl-L-tyrosine (e.g., $^{18}F$-FMT) and studied its biodistribution in hepatoma-bearing rats. See, Nuclear Medicine and Biology 31 (2004) 191-198. As shown, the tracer accumulated in the pancreas and there was a meaningful contrast achieved at sixty (60) minutes that afforded visualization of the tumor. However, there was some degree of defluorination noted, likely due to uptake of the tracer in the bone marrow. Defluorination of $^{18}F$-FMT contrasts with no defluorination of $^{18}F$-fluoroethyltyrosine (i.e., $^{18}F$-FET) an approved imaging tracer for high-grade glioma (See, 10.2967/jnumed.114.140608 and also NCT04001257). It is noted that an elevated uptake of the foregoing PET tracers in glioma and other tumor is mediated by LAT-1, the same large neutral amino acid transporter that mediates BPA uptake into head and neck, GBM, and melanoma lesions.

Based on the foregoing, the disclosure endeavors to develop syntheses of borylated tyrosine analogs to evaluate the expression of LAT-1 in selected cell lines and show that these borylated amino acid analogs are show uptake in cancer cell lines. Furthermore, it is demonstrated in the disclosure that the tyrosine analogs are taken up by FaDu established xenografts in immunodeficient mice in a dose-dependent fashion.

Accordingly, the utilization of borylated tyrosine as a neutron capture agent in certain cancers is contemplated by the present disclosure.

In one embodiment of the present disclosure, a BAA comprising tyrosine is denoted as BTS and has the following chemical formula set forth in FIG. 1.

In one embodiment of the present disclosure, a BAA comprising tyrosine is denoted as BTS(OMe) and has the following chemical formula set forth in FIG. 3.

The synthesis of BTS and BTS(OMe) present a challenge due to the O-hydroxyl of tyrosine in ortho-position to boronic acid. This hydroxyl is an electron-donating group, and it hampers the pinacol-borane deprotection step of the synthesis. As a result, known synthesis of BTS and BTS (OMe) results in low yield and difficult-to-remove impurities. Accordingly, it is an object of the present disclosure to provide a novel synthesis of BTS and BTS(OMe) that results high yield and purity at up to a one (1) gram scale.

By way of background, BTS and BTS(OMe) are very soluble in water. However, unlike BPA, the only boron carrier currently approved for use in BNCT, BTS does not require fructose to aid solubility. Additionally, BTS(OMe) does require fructose, however, the threshold of solubility is much higher compared to BPA. As a result, using BTS or BTS(OMe) versus BPA will allow for the administration of higher concentrations and smaller volumes of boron compounds than what is currently feasible with L-BPA fructose (or sorbitol) formulations. The clinical significance of being able to achieve higher boron concentration in a tumor will translate into higher efficacy of neutron irradiation in BNCT and/or PBFT therapy and ultimately, a lower rate of cancer recurrence.

Accordingly, it is an object of the present disclosure to teach a new and improved synthesis of BTS and BTS(OMe).

(c) New and Improved Synthesis of BTS and BTS(OMe)

The synthesis of BTS (as shown in FIG. 2) and BTS (OMe) (as shown in FIG. 4) are on a laboratory scale an efficient transformation. However, the formation of L-DOPA and Tyr has been observed following the traditional Miyaura coupling (i.e., Pd coupling of bis(pinacolato)diborane followed by NaIO$_4$ deprotection). The result is a major by-product (See, FIG. 7). Chromatography is required to remove the by-product.

In addition, the synthesis of BTS (as shown in FIG. 2) and BTS(OMe) (as shown in FIG. 4) does not progress when the N or C termini are deprotected unless excess BBr$_3$ is added. However, this presents a further problem in that the synthesis leads to rapid de-boration. It is also noted that initiating the synthesis at 0° C. also leads to de-boration.

Accordingly, it is an object of the present disclosure to enable novel synthesis methods for BTS and BTS(OMe) whereby the impurity generating by Pd coupling is eliminated (See, FIG. 6).

Additionally, it is an object of the present disclosure to enable novel synthesis methods for BTS and BTS(OMe) whereby the deprotection step is modified to avoid de-boration of BTS and BTS(OMe). (See, FIGS. 9 through 12).

The resulting novel synthesis is prepared using the chromatography conditions set forth in FIG. 13 and is analyzed using the using the chromatography conditions set forth in FIG. 7 and will produce BTS (as shown in FIG. 2) and BTS(OMe) (as shown in FIG. 4) and will allow for commercial scale-up to one (1) gram.

In a preferred embodiment, the invention comprises a synthesis of BTS and BTS(OMe) comprising the conversion of L-tyrosine to the target materials. The conversion of L-tyrosine to N-Boc-Tyr(3-Br, 4-MeO)—OMe is first presented in Ghosh, S. et al. ARKIVOC, 2009 (vii), 72-78.

The conversion of N-Boc-Tyr(3-Br, 4-MeO)—OMe to the aryl boronic acid N-Boc-Tyr(3-B(OH)$_2$-4-MeO)—OMe consists of a palladation followed by metal exchange to the required boronic acid. In a flame dried argon quench flask was charged with 30 mL of methanol and 12 mL of dimethoxyethane. To the solution was added 2.8 g of potassium acetate, then 5 g of Boc-Tyr(3-Br, 4-OMe)-OMe, followed by 1.3 g of tetrahydroxydiborane. Finally, to the reaction mixture is added catalytic Pd, 3 mg of Chloro[(tri-tert-butylphosphine)-2-(2-aminobiphenyl)]palladium (II). Under an argon atmosphere the reaction is stirred over night at 20° C. At the reactions completion 20 mL of water is slowly added, and allowed to quench for 30 min. The solids are removed via filtration. The organic solvents are then removed under reduced pressure. The aqueous layer is then washed three times with ethyl acetate. The organic layers are combined and concentrated under reduced pressure. The crude material is further purified via flash chromatography on silica at 25% ethyl acetate in hexanes. Upon removal of organic solvents, the target material is isolated at 75% yield as a white solid.

Following the introduction of boronic acid the synthesis diverges to form the compounds BTS and BTS(OMe). The selective saponification of N-Boc-Tyr(3-B(OH)$_2$-4-MeO)—OMe to N-Boc-Tyr(3-B(OH)$_2$-4-MeO)—OH is highlighted in Ghosh, S. et al. ARKIVOC, 2009 (vii), 72-78. Following the saponification is the removal of the tert-butyl carbamate to reveal the structure of BTS(OMe). To a flask charged with 1 g of N-Boc-Tyr(3-B(OH)$_2$, 4-OMe)-OH was added a solution of 4 M hydrochloric acid in dioxane. After one hour no presence of the Boc protected starting material was observable. The volatile solvent and acid were removed under reduced pressure, and the target material was purified via preparative LC.

As for the revealing of BTS a two-step process from N-Boc-Tyr(3-B(OH)$_2$-4-MeO)—OMe is followed. In a flame dried argon quench flask was charged with 25 mL of dichloromethane. To the solution was added 1.5 g of N-Boc-Tyr(3-B(OH)$_2$, 4-OMe)-OMe. The temperature was reduced to −78° C. with a dry ice bath. One equivalent of boron tribromide was added. After 30 min the Boc group is no longer observable by LCMS, at this point a second equivalent of boron tribromide is added. The reaction is allowed to warm to 0° C. After 2 h the phenolic oxygen is demethylated. The reaction is quenched with water, and the DCM is removed via extraction. The aqueous layer is brought to greater than pH 10 with LiOH. After 15 min at high pH the ester is saponified providing the target material. The aqueous layer is concentrated under reduced pressure, and the final material is isolated via preparative liquid chromatography.

VII.) Boron Neutron Capture Therapy Using BTS & BTS(OMe)

One aspect of the present disclosure is the use of BTS and BTS(OMe) as a modality for Boron Neutron Capture Therapy (BNCT) and/or Boron Proton Capture Therapy ("BPCT"). Briefly, BNCT is a binary treatment modality in which neither component alone is lethal or toxic to the tumor. The two components comprise (i) the infusion or delivery of a capture compound, which preferentially is concentrated in the tumor, and (ii) the irradiation of the tumor site by neutrons or by protons. In BNCT, given the large cross-section of thermal neutron interactions with $^{10}$B, there is consequently a high probability of a splitting of Boron nucleus into $^4$He$^{2+}$ and $^7$Li$^+$. Given that the ionization capability of He$^{2+}$ and Li$^+$ is high, and the distances travelled are short, then the cells preferably enriched by Boron are killed and the healthy cells are damaged much less due to the lack of high concentration of boron. Given this, the advantage of BNCT is the destruction of tumor cells without a highly traumatic surgical procedure. However, as will be understood by one of skill in the art, success is predicated high concentration and selective localization of $^{10}$B in tumor cells.

In one embodiment, $^{10}$B is concentrated on BTS and/or BTS(OMe). The BTS and/or BTS(OMe) is then given to a patient and the BTS & BTS(OMe) is localized into a tumor cell. The BTS & BTS(OMe) containing $^{10}$B are concentrated into the tumor and the tumor is irradiated using epithermal neutrons. The tumor cells are destroyed.

VIII. Proton Boron Fusion Therapy Using BAAs

Another aspect of the present disclosure is the use of BTS & BTS(OMe) as a modality for Proton Boron Fusion Therapy (PBFT). Briefly, the proton boron fusion reaction was introduced in the 1960s. Three alpha particles are emitted after the reaction between a proton ($^1$H) and a boron particle) These three alpha particles provide the damage to the tumor cell, just as in the case of alpha particles in BNCT. Theoretically, in the case of PBFT, the therapy efficacy per incident particle is three times (3×) greater than that of BNCT. In addition, because the proton beam has the advantage of a Bragg-peak characteristic, normal tissue damage can be reduced. Generally speaking, many studies for tumor treatment using alpha particles have been performed. In order to take advantage of alpha particles for dose delivery, two key points should be considered. First, the boron uptake should be labeled accurately to the target cell. As mentioned previously, alpha particles are generated where the boronate compound is accumulated. If this happens in normal tissue near the tumor region, alpha particles will damage the normal tissue as well as the tumor cell. Second, the number of generated alpha particles is also a significant factor for effective therapy. By using PBFT, a more effective therapy can be realized compared to BNCT or conventional proton therapy alone.

In one embodiment, $^{10}$B and/or $^{11}$B is concentrated on a BTS & BTS(OMe). The BTS & BTS(OMe) is then given to a patient and the BTS & BTS(OMe) is localized into a tumor cell. The BTS & BTS(OMe) containing $^{10}$B and/or $^{11}$B are concentrated into the tumor and the tumor is irradiated using epithermal neutrons. The tumor cells are destroyed.

IX. Methods of Delivering BTS & BTS(OMe) to a Cell

As will be appreciated by one of ordinary skill in the art, the ability to efficiently deliver high concentrations of Boron to a cell is an advantage of the present invention.

It is shown that the BTS & BTS(OMe) of the present disclosure enables a higher amount of boron to be administered to a cell safely in mammals. Briefly, BTS & BTS (OMe) of the disclosure are prepared as set forth in the disclosure. The resulting BTS & BTS(OMe) are taken up by the tumor cell by the upregulated LAT-1 transporter protein.

X.) Kits/Articles of Manufacture

For use in the laboratory, prognostic, prophylactic, diagnostic, and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a BTS & BTS(OMe) or several BTS(s) & BTS(OMe)(s) of the disclosure. Kits can comprise a container comprising a drug unit. The kit can include all or part of the BTS(s) & BTS(OMe)(s) and/or diagnostic assays for detecting cancer and/or other immunological disorders.

The kit of the invention will typically comprise the container described above, and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic, or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing, or prognosing a condition, such as a cancer or other immunological disorder.

The terms "kit" and "article of manufacture" can be used as synonyms.

In another embodiment of the invention, an article(s) of manufacture containing compositions, such as BTS(s) & BTS(OMe)(s) of the disclosure. The article of manufacture typically comprises at least one container and at least one label. Suitable containers include, for example, bottles, vials, syringes, and test tubes. The containers can be formed from a variety of materials such as glass, metal, or plastic. The container can hold one or several BTS(s) & BTS (OMe) (s) and/or one or more therapeutics doses of BTS(s) & BTS (OMe) (s).

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a BTS & BTS (OMe) of the present disclosure.

The article of manufacture can further comprise a second container comprising a pharmaceutically acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXEMPLARY EMBODIMENTS

1) A composition comprising a chemical structure as follows:

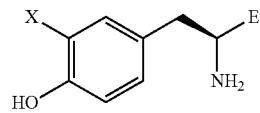

Where E=CO$_2$H, CONHB$_{12}$H$_{11}$, B(OH)$_2$; and
X=H, B(OH)$_2$, Bpin, (—O—CH$_2$CH$_2$)$_2$—O—B$_{12}$H$_{11}$, or BF$_3$-.

2) A composition comprising a chemical structure as follows:

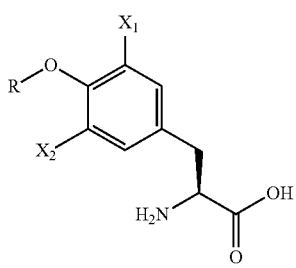

Where:
R=H, CH$_3$, or CF$_3$;
X$_1$=H, B(OH)$_2$, or BF$_3$-; and
X$_2$=H, B(OH)$_2$, or BF$_3$-

3) The composition of claim 2, wherein the composition comprises:

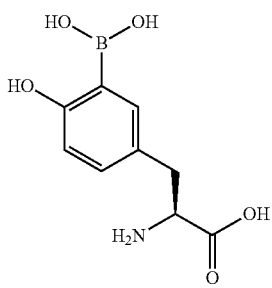 [SMILES: N[C@@H](Cc1ccc(O)c(B(O)O)c1)C(=O)O]

4) A composition of claim 2. Wherein the composition comprises:

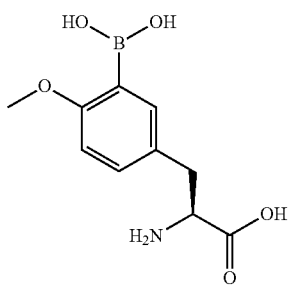 [SMILES: COc1ccc(C[C@H](N)C(=O)O)cc1B(O)O]

5) A composition produced by a method of conversion of L-tyrosine to a target material, comprising:
  (i) Conversion of N-Boc-Tyr(3-Br, 4-MeO)—OMe (4) to the aryl boronic acid N-Boc-Tyr(3-B(OH)$_{2-4}$-MeO)—OMe (5) which comprises a palladation followed by a metal exchange to the required boronic acid comprising the following:
    a. a solvent mixture comprising methanol and dimethoxyethane;
    b. a ligand substituent comprising potassium acetate;
    c. a reagent of type aryl bromide comprising N-Boc-Tyr(3-Br, 4-MeO)—OMe (4);
    d. a boronating agent comprising tetrahydroxyborane;
    e. a palladium catalyst comprising chloro((tir-tert-butylphosphine)-2-(2-aminobiphenyl))palladium (II); and
    f. a purification comprising (i) quenching with water, (ii) a solvent exchange comprising ethyl acetate, and (iii) a flash chromatography on silica with approximately 25% ethyl acetate in hexanes.
  (ii) Following the introduction of boronic acid, the synthesis diverges to form the compounds BTS (7) and BTS(OMe) (9).
  (iii) Conversion N-Boc-Tyr(3-B(OH)$_2$-4-MeO)—OH (8) to reveal the structure of BTS(OMe) (9) comprising:
    a. a solution comprising 4 M hydrochloric acid in dioxane;
    b. a reagent of type tertbutylcarbamate comprising, N-Boc-Tyr(3-B(OH)2, 4-OMe)-OH; and
    c. a purification comprising a reverse phase chromatography with a range of 0% to 20% acetonitrile in water.
  (iv) Conversion of N-Boc-Tyr(3-B(OH)$_2$, 4-MeO)—OMe (5) to BTS (7) which comprises a simultaneous methyl ether cleavage and carbamate removal subsequently followed by saponification comprising:
    a. a solution comprising dichloromethane;
    b. an added reagent comprising N-Boc-Tyr(3-B(OH)$_2$, 4-MeO)—OMe (5);
    c. a reactant comprising boron tribromide;
    d. a solvent exchange from dichloromethane to water;
    e. a reactant comprising LiOH; and
    f. a purification comprising a reverse phase chromatography with a range of 0% to 20% acetonitrile in water.

6) The method of claim 5, wherein the composition is BTS.

7) The method of claim 5, wherein the composition of BTS(OMe).

8) A method for producing BTS comprising a synthesis shown substantially in FIG. 2.

9) A method for producing BTS(OMe) comprising a synthesis shown substantially in FIG. 4.

10) A method of purifying a compound shown in FIG. 6, wherein the purification method comprises the steps shown in FIG. 8.

11) The method of claim 10, whereby the purification modification comprises:
  (i) a substitution of dimethoxyethane (DME) for ethylene glycol in the reaction;
  (ii) removal of organic solvents via reduced pressure, then extract target material from aqueous into ethyl acetate; and
  (iii) a purification flash chromatography isocratic at 30% EtOAc in hexanes.

12) A method of deprotection comprising the synthesis of FIG. 11.

13) The method of claim 12, wherein the deprotection step reduces impurities in a target material.

14) The method of claim 13, wherein the target material is BTS.

15) The method of claim 13, wherein the target material is BTS(OMe).

16) A method comprising, a synthesis of N-Boc-Tyr(3-B(OH)$_2$), (4-OMe)-OH to BTS as set forth in FIG. 9 comprising a further synthesis modification comprising a procedure for demethylation with BBr$_3$ as set forth in FIG. 12.

17) The method of claim 16, wherein the demethylation with BBr$_3$ mitigates de-boration of a target material.

18) The method of claim 17, wherein the target material is BTS.

19) The method of claim 17, wherein the target material is BTS(OMe).

20) A kit comprising the composition of claim 1.
21) A kit comprising the composition of claim 2.
22) A kit comprising the composition of claim 3.
23) A kit comprising the composition of claim 4.
24) A Dosage Unit Form comprising a composition of claim 1.
25) A Dosage Unit Form comprising a composition of claim 2.
26) A Dosage Unit Form comprising a composition of claim 3.
27) A Dosage Unit Form comprising a composition of claim 4.
28) The Human Unit Form of claim 24, wherein the Human Unit Form is used in Boron Neutron Capture Therapy (BNCT).
29) The Human Unit Form of claim 25, wherein the Human Unit Form is used in Boron Neutron Capture Therapy (BNCT).
30) The Human Unit Form of claim 26, wherein the Human Unit Form is used in Boron Neutron Capture Therapy (BNCT).
31) The Human Unit Form of claim 27, wherein the Human Unit Form is used in Boron Neutron Capture Therapy (BNCT).
32) A BTS compound produced by the method of claim 5.
33) A BTS(OMe) compound produced by the method of claim 5.
34) A method of treating cancer using a BTS compound of claim 32, wherein said BTS is used as a neutron capture agent in BNCT.
35) A method of treating cancer using a BTS(OMe) compound of claim 33, wherein said BTS is used as a neutron capture agent in BNCT.

EXAMPLES

Various aspects of the invention are further described and illustrated by way of the several examples that follow, none of which is intended to limit the scope of the invention.

Example 1: Synthesis of Boc-Tyr(3-Br, 4-OMe)-OMe Precursor

The synthesis of the N-Boc-Tyr(3-Br, 4-OMe)-OMe precursor is shown in FIG. 5 and is performed using standard methods. See, GHOSH, et. al., Arkivoc (2009) (vii) pp. 72-78.

Example 2: Synthesis of Tyr to Boc-Tyr(3-Br, 4-OMe)-OMe to Boc-Tyr(3-B(OH)$_2$, 4-OMe)-OMe Following the synthesis of the N-Boc-Tyr(3-Br, 4-OMe)-OMe precursor (See, Example 1, supra), a further synthesis to N-Boc-Tyr(3-B(OH)$_2$, 4-OMe)-OMe was performed using the following methods. See, GURUNG, et. al., Org. Process Res. Dev. (2017), 21, pp. 65-74.

Briefly, a flame dried argon quench flask was charged with 30 mL of methanol and 12 mL of dimethoxyethane. Then, to the solution was added 2.8 g of potassium acetate, followed by 5 g of N-Boc-Tyr(3-Br, 4-OMe)-OMe, followed by 1.3 g of tetrahydroxydiborane. Finally, to the reaction mixture is added catalytic Pd, 3 mg of Chloro[(tri-tert-butylphosphine)-2-(2-aminobiphenyl)]palladium (II). Under an argon atmosphere the reaction is stirred over night at 20° C. At the reactions completion 20 mL of water is slowly added, and allowed to quench for 30 min. The solids are removed via filtration. The organic solvents are then removed under reduced pressure. The aqueous layer is then washed three (3) times with ethyl acetate. Then the organic layers are combined and concentrated under reduced pressure. The crude material is further purified via flash chromatography on silica at 25% ethyl acetate in hexanes. Upon removal of organic solvents, the target material is isolated at 75% yield as a white solid.

It is observed that the target material does not precipitate out in the synthesis noted herein, but it remains in the mother liquor following filtration. According, the disclosure further modifies the purification as follows:
 (i) Substitute dimethoxyethane (DME) for ethylene glycol in the reaction.
It is noted and understood that the reaction maintains chelation but has a lower boiling point that was previously known in the art.
 (ii) Following initial filtration, remove organic solvents via reduced pressure, then extract target material from aqueous into ethyl acetate.
It is noted that this additional step provides the benefit of back extraction into an organic phase which removes hydrophilic impurities that was not previously reported in the art.
 (iii) A diphenyl-boronic acid is the major impurity/byproduct, increased dilution of reaction shows a minor reduction in this material.
It is noted that the increase dilution favors the borylation over the aryl-aryl palladium coupling by taking advantage of the higher equivalency of BBA and reducing the probability of interactions between the aryl-palladium complex with the distinctive coupling partner N-Boc-Tyr(3-B(OH)$_2$, 4-OMe)-OMe.
 (iv) Finally, for further purification flash chromatography isocratic at 30% EtOAc in hexanes is performed.
It is noted that the purification at 25% EtOAc in hexanes provides the benefit of separating the closely eluting N-Boc-Tyr(3-B(OH)$_2$, 4-OMe)-OMe from the biaryl byproduct.

The resulting modified procedure set forth in FIG. 6 is performed to achieve the resulting compound shown in FIG. 6 (Chemical Structure No. 5).

Example 3: Analysis of Pd Coupling Using QDA Mass Detection

To show the impurities that result from PD coupling in the synthesis set forth in Example 2, supra, the following experiment was performed using QDA Mass Detection. Briefly, the QDA mass detector assay was used according to the manufacturers standard protocol. The column was an Acquity BEH C18 column (2.1×50 mm) with Guard Column (Waters Corp., Milford, MA). The column temperature was 40° C. Mobile Phase A comprised 0.1% Formic Acid and Mobile Phase B comprised 0.1% Formic Acid and 90% acetonitrile, The gradient is set forth in the following table:

| Minute | % A | % B |
| --- | --- | --- |
| 0.0 | 98 | 2 |
| 0.3 | 98 | 2 |
| 6.0 | 80 | 20 |
| 6.7 | 80 | 20 |
| 6.8 | 5 | 95 |
| 7.5 | 5 | 95 |
| 7.7 | 98 | 2 |

It should be noted that the positive ion mode on the QDA mass detector does not show the Boc groups, and they are purposefully omitted in the structures to show mass equivalency in a more straightforward manner.

The results set forth in FIG. 7(A) show the total ion current (TIC) of the reaction (See, Example 2, supra). Note, TIC chromatogram represents the summed intensity across the entire range of masses being detected at every point in the analysis. FIG. 7(B) shows the UV trace at 285 nm. Finally, FIG. 7(C) shows the mass ID of the product and the major impurity associated with the reaction prior to the synthesis modification set forth in FIG. 6. The results show the target material eluting at 2.0 min while the impurity is shown at 2.7 min. It is observed that a unique feature of the impurity is that the impurity maintains a one boronic acid motif, even though that feature does not survive the deprotections of the N and C termini.

Example 4: Chemical Synthesis for Boc-Tyr(3-B(OH)$_2$, 4-OMe)-OMe Deprotection Following the novel purification procedure set forth in Example 2, supra, to decrease the impurities found in the target material, an additional deprotection step is performed in the synthesis. This deprotection step is a further novel modification to the synthesis of BTS and BTS(OMe) and is performed in the following manner.

Briefly, a flame dried argon quench flask is charged with 25 mL of dichloromethane. To the solution was added 1.5 g of N-Boc-Tyr(3-B(OH)$_2$, 4-OMe)-OMe. The temperature was reduced to −78° C. with a dry ice bath. One equivalent of boron tribromide was added. Then, after thirty (30) min. the Boc group is no longer observable by LCMS. Accordingly, at this stage, a second equivalent of boron tribromide is added. The reaction is allowed to warm to 0° C. After two (2) hrs., the phenolic oxygen is demethylated. The reaction is then quenched with water, and the DCM is removed via extraction. The aqueous layer is brought to greater than pH 10 with LION. After fifteen (15) min. at a pH>10<12 the ester is saponified providing the target material. The aqueous layer is concentrated under reduced pressure, and the final material is isolated via preparative liquid chromatography.

It is observed that the reaction does not seem to progress when the N or C termini are deprotected, except when excess BBr$_3$ is added. However, this leads to rapid de-boration. The de-boration of the reaction is problematic because either the substrate is returned to the tyrosine scaffold via protonation or oxidized to the 3,4-dyhydroxy tyrosine, L-DOPA. Both of which no longer carrier the necessary boron required for BNCT.

Accordingly, it has been observed, and is within an aspect of the disclosure, that the reaction is efficient and advantageous for commercial scale up following the addition of 1 equivalent of BBr$_3$ and monitoring the reaction until the Boc group is removed (approximately 30 min.) and then adding the second equivalent of BBr$_3$. After the addition of the second equivalent of BBr$_3$, the reaction is warmed up to 0° C. to speed up the reaction (approximately two (2) hrs.). In an alternative embodiment, it is within the aspect of the disclosure to perform a steady addition of BBr$_3$ over the course of the reaction versus utilizing two (2) equivalent additions, as set forth herein.

Finally, it is noted that since the target material is soluble in water, once the reaction is quenched with water as set forth herein, this allows for the extraction from DCM into water and the telescoping of the material directly into the final saponification reaction. It will be readily apparent to one of skill in the art that if the mixture is allowed to sit in water for too long, HBr is formed and initiates protodeboronation which is an undesired side reaction.

The results of the synthesis set forth herein are set forth in FIG. 8.

Rather than the in-situ complete deprotection shown in FIG. 8, the deprotection can be done in a stepwise fashion. Briefly, a flame dried argon quench flask is charged with 25 mL of dichloromethane. To the solution was added 1.5 g of N-Boc-Tyr(3-B(OH)$_2$, 4-OMe)-OMe. The temperature was reduced to 0° C. with a dry ice bath. One equivalent of boron tribromide was added. Then, after thirty (30) min the Boc group is no longer observable by LCMS. Accordingly, at this stage, a second equivalent of boron tribromide is added. The reaction is maintained at 0° C. After two (2) hrs., the phenolic oxygen is demethylated. The reaction is then quenched with methanol, and the organic solvents are removed under reduced pressure leaving a yellow powder. To this powder is added acetonitrile which precipitates the target material as a white powder.

The results of the synthesis set forth herein are set forth in FIG. 9.

The saponification step is found to be extremely sensitive, and most conditions lead to either prot-de-boration to tyrosine, or oxidative de-boration leading to L-DOPA. Two successful paths have been found.

In the first example Tyr(3-B(OH)$_2$—OMe is dissolved in 10 volumes of 0.1 M KCl in water, the pH is adjusted to 7 using 0.1 M NaOH. To this solution is added pig liver esterase, and the reaction is brought to 37° C. After 2 days the target material, Tyr(3-B(OH)2 is isolated via preparative LCMS. The second method is done by dissolving Tyr(3-B(OH)$_2$—OMe in 60 volumes of water. To this solution is added 2.2 equivalents of LION. Within 15 minutes the saponified material is ready for purification via preparative LCMS.

The results of the synthesis set forth herein are set forth in FIGS. 10(A) and 10(B) respectively.

Example 5: Chemical Synthesis for Boc-Tyr(3-B(OH)$_2$, 4-OMe)-OMe to Boc-Tyr(3-B(OH)$_2$, 4-OMe)-OH The synthesis of N-Boc-Tyr(3-B(OH)$_2$, 4-OMe)-OMe to N-Boc-Tyr(3-B(OH)$_2$, 4-OMe)-OH is shown in FIG. 11 and is performed using standard methods. See, GHOSH, et. al., Arkivoc (2009) (vii) pp. 72-78.

Example 6: Chemical Synthesis for Boc-Tyr(3-B(OH)$_2$, 4-OMe)-OH to BTS(OMe)

The synthesis of N-Boc-Tyr(3-B(OH)$_2$, 4-OMe)-OH to BTS(OMe) is shown in FIG. 12 and utilizes a further synthesis modification that is within the scope of this disclosure. The modification does not utilize a procedure for demethylation with BBr$_3$ and is shown in FIG. 8 and FIG. 9, so as to maintain the methyl ether.

Briefly, to a flask charged with 1.0 g of N-Boc-Tyr(3-B(OH)$_2$, 4-Ome)-OH was added a solution of 4 M hydrochloric acid in dioxane. After one (1) hr. no presence of the Boc protected starting material was observable. The volatile solvent and acid were removed under reduced pressure, and the target material was purified via preparative LC using the protocol. Briefly, a C18 preparative column was used with dimensions of 30 mm×100 mm. The flow was set at 50 mL/min. The gradient used was set forth in the following table:

| Minute | % A | % B |
| --- | --- | --- |
| 0.0 | 100 | 0 |
| 0.75 | 100 | 0 |
| 19.0 | 80 | 20 |
| 20.0 | 80 | 20 |
| 20.1 | 80 | 20 |

The result of the chromatography analysis is set forth in FIG. 13. The resulting BTS(OMe) has the structure set forth in FIG. 3.

Example 7: LAT1 Expression Analysis Via Western Blot

By way of brief background, LAT-1 (SLC7A5) is an amino acid transporter that mediates uptake of large neutral amino acids including Leu, Phe, Tyr, His and Trp. It is also responsible for uptake of L-DOPA and thyroid hormones. Structurally, it is an 11-TM protein that forms a heterodimer with CD98. Its expression is upregulated in certain cancer indications including cancer of the head and neck and gliomas.

LAT-1 expression was qualitatively estimated across cell lines using Western blotting. Briefly, cell lysates (10 μg of total protein) were run on SDS-PAGE and transferred to PVDF membrane. Anti-SLC7A5 polyclonal, (Invitrogen #PA5-50485) were used for the detection of LAT-1. Mouse anti-b-actin MAb (Invitrogen #AM4302) was used as a loading control. Secondary (detection antibody) were Alexa Fluor Plus goat anti-rabbit and Alexa Fluor 790 donkey anti-mouse, respectively.

The results show cell lines FaDu, HeLa, and A431 exhibited the highest level of LAT-1 expression. (FIG. 14).

Accordingly, FaDu cell line (pharyngeal squamous carcinoma) was chosen for the subsequent evaluation of boronated amino acids because it represents the indication most relevant to Boron Neutron Capture Therapy (BNCT) treatment.

Example 8: Impurity Profiles of BTS, BTS(OMe) Solutions

To determine the solubility and impurity profiles of BTS and BTS(OMe) in solution, the following experiments were performed using the following protocols. Briefly, BTS test article preparation(s) were prepared by dissolving in water and adjusting pH to 7-7.5 by NaOH.

BTS(OMe) test article preparation(s) were prepared by dissolving in water and gradually raising pH by adding NaOH until all the crystals are solubilized. The pH at that point is approximately 9.5-10. Fructose is then added at the ratio of 1.1 mol/mol BTS(OMe). The pH is adjusted to 7-7.5 using concentrated HCl.

Both solutions were adjusted to 100 mg/mL and 0.2 μm filtered. The actual concentrations are confirmed by ICP OES.

The analysis of the BTS and BTS(OMe) solutions were carried out via LCMS. Briefly, LS/MS purity confirmation was carried out by LCMS using Acquity H-class system (Waters) equipped with Acquity BEH C18 column (50×2.1 mm, 1.7 μm, (Waters)) held at 40° C. and equilibrated with aqueous formic acid-2% acetonitrile. The compound and impurities were eluted using a gradient of acetonitrile-formic acid from 2 to 20% over 6 min. The peak assignment was carried out using an in-line ESI LCMS in the positive mode. The results show both compounds were greater than 95% free of impurities. (FIG. 15).

Example 9: Boron Uptake in FaDu and CT26 Cells In Vitro

It has been widely demonstrated that hypopharengial squamous carcinoma-derived cell line FaDu has high LAT-1 expression. As a result, it accumulates boron compounds at significant levels. Additionally, FaDu also grows well as an established xenograft model in SCID mice. This disclosure endeavored to determine whether a mouse-derived cancer cell line, CT-26, is suitable for BNCT experiments. By way of background, CT26 is a syngeneic model, it can be implanted and established in wild-type BalbC mice and provides a convenient and low-cost model.

Briefly, CT26 cells were harvested and washed with PBS two (2) times, and the count was adjusted 2 million/ml in HBSS media Boron compounds were then added to cells at the final concentration of 2.5 mM in HBSS and the cells were incubated at 37° C. in a humidified 5% $CO_2$ atmosphere for 2.0 hrs. with shaking. Following a two (2) hr. incubation, cells were harvested and washed two times with ice cold PBS. Cells were suspended in 1 ml ice cold PBS and a portion (50 NI) was lysed in RIPA buffer and protein content was determined by BCA assay.

The remaining portion (950 NI) was subjected to nitric acid lysis (66.7% acid at 80° C.) and boron measurements were carried out using ICP-OES.

The results in FIG. 16 show that when cells were incubated in media containing equimolar concentrations for each of the three compounds, the intracellular boron concentration was 60% higher for the cells treated with BTS compared to BPA-fructose (1700±133 vs 1097±59 μg/g). The intracellular concentration of BTS(OMe)-fructose was similar to that of BPA-fructose, 1005±113 μg/g. There are several possibilities to account for the fact that BTS is the preferred substrate for FaDu cells. First, other transporter besides LAT-1 (i.e., SLC7A5) may be involved resulting in an augmented net intracellular boron. Alternatively, BTS may be retained better inside the cells since amino acid transporters work in both directions. We have previously shown that a pan-LAT-1 inhibitor BCH (2-aminobicyclo-(2,2,1)-heptane-2-carboxylic acid) as well as a LAT-1 specific inhibitor JPH203 diminished boron accumulations in a concentration-dependent fashion suggesting that LAT-1 is likely to be the sole transporter for borylated tyrosine analogs (unpublished). We have also showed that there is a difference between BPA and BTS in cellular retention, i.e., intracellular boron concentration reduction once boron source is removed from the media. The amount of intracellular boron decreases sharply for cells treated with BPA-fructose once BPA is removed and replaced with fresh medium.

In the CT26 cell line the amount of each compound internalized is approximately 40% less than in FaDu while the decrease in the internalization of BTS was more pronounced. Low expression of LAT-1 in CT26 estimated by Western blot is consistent with the overall reduced boron uptake. Each bar represents three (3) independent experiments performed on different days (FaDu) or a single experiment (CT-26) Error bars represent 1 standard deviation. Boronophenylalanine (as fructose solution) was used as a control. (See, FIG. 14).

Example 10: BTS Uptake Across Multiple Head and Neck Cancer Cells Lines

To evaluate the uptake of BTS in multiple head and neck cancer cell lines as well as melanoma cell lines the following experiments were performed using the following protocols.

Briefly, five (5) human-derived cell lines (FaDu, A375, SCC-25, A253, and Detroit 562), all representing cancer indications relevant to BNCT treatment, were cultured, and treated with either BPA-fructose (the standard of care) or with BTS for two (2) hours. The cells were then washed to remove the compounds, harvested, and treated as per the protocol described above. Boron uptake was reported as µg boron per mg of cellular protein as determined by ICP OES and by the BCA assay, respectively.

The results show that BTS has a superior uptake when compared to BPA-fructose across each of the cell lines tested. See, FIG. 17.

Example 11: BTS Uptake Using Rat Glioma Cell Lines

Rat glioma cell lines were extensively used as orthotopic cancer models to conduct reactor based BNCT studies using either innovative boron carriers or a myriad of ways to enhance the uptake of BPA, including convection enhanced delivery of boronoporphyrins (Yang, et al., doi:10.1016/j.apradiso.2014.01.002), or pre-treatment of tumors with L-DOPA (Barth, et al., J Neurooncol. 2009; 94:299-312).

In this experiment, used cultured cell lines to confirm that BTS can be used for efficient boron delivery into both F98 and C6 rat glioma cell lines. Indeed, the boron concentration achieved at 2 hr. was >2-fold higher with BTS compared to BPA-fructose demonstrating that BTS is the preferred LAT-1 substrate for multiple cancer indications even across multiple species (See FIG. 18). This compound is expected to cross BBB and will be relevant for BNCT of brain tumors.

Example 12: Competition Between BTS and Phe for LAT1

To determine the ability for BTS and BTS(OMe) to mediate LAT-1, the following experiments were performed using the following protocols. Briefly, FaDu cells (2 million) were incubated in HBSS medium for two (2) hrs. at 37° C. with 0.5 mM of either (i) BTS, (ii) BTS(OMe), or (iii) BPA-fructose in the absence (19A) or presence of increasing concentrations of LAT-1 specific inhibitor JPH203-dichloride, (19A) or phenylalanine, a competitor (19B). Following incubation, the cells were harvested and washed with cold PBS. The amount of each compound that was taken up by the cells was determined by ICP OES. The $IC_{50}$ determination was made by a three (3) parameter inhibitor non-linear regression fit using Prism (Graph Pad) software.

The results show that the BPA, BTS, and BTS(OMe) transport is equally inhibited by JHP203 with an IC50 of approx. 0.3 mM. This indicates LAT-1 mediated uptake.

In the competition assay, increased concentration of Phe in the range of 0.01 to 20 mM was used. It is shown that BTS has a higher IC50 compared to either BTS(OMe) or BPA which indicates that higher phenylalanine concentration is required to outcompete the former. This suggests that BTS has a higher affinity for LAT-1. (FIG. 19).

Example 12: Pharmacokinetics of BTS Versus BPA in Non-Tumor Bearing Balb-C Mice To determine the pharmacokinetics of BTS versus BPA (BPA-fructose) in blood, the following experiments were performed using the following protocols and under the parameters set forth in Table II. Briefly, 200 mg/mL of each compound (BTA and BPA-fructose) was injected into the tail vein of Balb/C non-tumor bearing male mice (5 mice per group). Blood was drawn at the following time points: 2, 5, 16, 30, 60, 120 and 240 min into EDTA-coated tubes. Boron concentration was measured using ICP OES following the digestion in concentrated nitric acid for one (1) hr. The boron concentration was normalized to 1 mL of blood and plotted using GraphPad Prizm. The PK parameters (see 20(B)) were obtain using PK Solver version 2.0 using compartmental analysis. BPA-fructose was used as a reference substance.

The results show that BTS (as a saline formulation) exhibited bi-phasic pharmacokinetics with shorter $t_{1/2}$ beta (e.g., elimination phase) and faster clearance (CL). The $t_{1/2}$ for BTS and BPA are reported but a rapid decline was observed during the alpha phase. The volume of distribution at the steady state (Vss) is lower for BTS than for BPA. This suggests that BTS has higher blood protein binding and is likely to be readily accessible to eliminating organs. (FIG. 20)

Example 13: BTS and BTS(OMe) Biodistribution Studies and Tumor to Blood Ratio(s) In Vivo To determine the biodistribution of BTS and BTS(OMe) and the tumor to blood ration, the following experiments were performed using the following protocols. Briefly, all compounds tested, with the exception of BPA, were prepared as 100 mg/mL stocks. BPA was prepared as a fructose solution at 25 mg/ml. The concentrations were confirmed by ICP OES prior to the study. The blood and tissues (tumor, kidney, and pancreas) were harvested at the times indicated, weighed, and placed inside the Teflon containers and digested using a CEM microwave oven. The digested tissues were analyzed by ICP OES to determine the boron concentration.

All animal studies were carried out following the "Guide for the care and use the laboratory animals," Eighth Edition and Animal Welfare Act (USDA). Briefly, human hypopharyngeal squamous cell carcinoma FaDu cells were maintained in DMEM, supplemented with L-glutamine and 10% FBS. Subcutaneous (s.c.) tumors were generated by injection of $2.5 \times 10^6$ cancer cells mixed at a 1:1 dilution with Matrigel (Corning Life Sciences) in the right flank of female CB17 SCID mice. Tumor sizes were determined by caliper measurements, and the tumor volume was calculated as $width^2 \times Length/2$, wherein width is the smallest dimension and length is the largest dimension. Tumors were allowed to grow untreated until they reached an approximate volume of 300 mm³. At that point, animals were randomized and allocated to each treatment group based on tumor volume at the time of treatment initiation to ensure similar mean tumor size and variation in each group.

Each group received a single dose of BPA at 200 mg/mg or a test article at either 400 mg/kg or 800 mg/mg via intravenous tail vein injection. The injection volume did not exceed 200 µL per mouse in concord with veterinary guidelines. Two (2) hrs. post dose, blood was collected from each mouse from the submandibular vein into K2 EDTA coated tubes. Tumor and organs were collected for boron analysis.

In order to determine the biodistribution of BTS and BTS(OMe) in FaDu-tumor bearing mice and determine the most appropriate time to harvest the tumor and organs of interest during the subsequent dose-escalation studies, 400 mg/kg doses of both molecules were administered as a bolus i.v. injection. BPA-fructose was administered at a dose of 200 mg/mL due to its solubility constraints and the requirements for the maximum i.v. volume allowed. The boron compound accumulation in blood/organs was determined by ICP OES and expressed as µg boron per gram of tissue.

The results show there was a significant accumulation in the tumor with maximum at sixty (60) min. and gradually tapering off at the later time points (FIG. 21(A)). In blood and kidney there was a rapid decline observed from the initial time point of 5 min. Notably, the decline was considerably slower for BTS in the kidney (FIG. 21(B) and FIG. 21(D)). That is either due to high kidney retention in glomellurus or possibly due to some reabsorption mechanism in nephrons. BTS also exhibited an exceedingly high uptake in murine pancreas plausibly due to the presence of LAT-1. (FIG. 21(C)). The high uptake of tyrosine-based PET tracers in murine pancreas has been shown (See, A B E, et al. 2009, https://doi.org/10.1080/02841850600979055).

Additionally, BTS(OMe) was remarkably similar in its biodistribution to BPA. The tumor to blood ratios for BTS increased more than two-fold between thirty (30) and sixty (60) min. and less than 30% between sixty (60) and one-hundred and twenty (120) min. (FIG. 22). Hence, the 120 min time point was chosen for the subsequent organ harvest in the subsequent studies.

Example 14: Biodistribution Studies and Boron Uptake of BTS and BTS(OMe) Using FaDu Cells In Vivo To determine the biodistribution and boron uptake of BTS and BTS(OMe) in vivo, the following experiments were performed using the following protocols. Briefly, to evaluate the effect of increased dose level using bolus i.v. injection on the accumulation of boron in the tumor, SCID mice carrying subcutaneous FaDu were dosed with BTS and BTS(OMe) at the levels ranging from 400 to 1000 mg/kg.

The tumor and selected organs were harvested at two (2) hr. post injection and processed for ICP OES.

The results of biodistribution are graphed (FIG. 23) and the tumor only is shown on the boron uptake (FIG. 24). The results concluded that both compounds BTS and BTS(OMe) accumulated in the tumor at considerably higher levels compared to the BPA group dosed at the 200 mg/kg level only. The low level of BPA dosing is the result of its solubility limits. The BTS group has achieved the level of boron in the tumor considerably exceeding the levels achievable using BPA (66±20 versus 25±3 µg/mg). The intratumoral boron concentration imparted by BTS(OMe), 44±8 µg/mg, was lower than BTS but still nearly twice as high as the level achieved with BPA. Both the BTS and BTS(OMe) levels increased only marginally from 800 to 1000 mg/kg dose-levels suggesting that the LAT-1 system is reaching saturation at approximately 800 mg/kg.

The results further confirmed that BTS(OMe) does not accumulate in either the kidney or pancreas and in that aspect is similar to BPA. The study also revealed that neither compound accumulates in the brain. Consistent with the previous pharmacokinetics studies (See, Example 12), all compounds are detectable in the blood at two (2) hrs. albeit at low levels. This suggests that the boron levels in the normal brain is likely to be the natural boron uptake and not confounded by the systemic presence of these compounds. Accordingly, the two (2) hr. post injection was correctly selected to represent biodistribution.

Example 15: Boron Delivery to Tumors Using Established Xenografts Chosen from the Indications Relevant to BNCT In a further experiment, to ascertain whether BTS and BTS(OMe) are taken up to a relatively higher degree across cancer multiple cell lines which results in a higher boron concentration, the following protocol was used. Briefly, a panel of five (5) human cancer cell lines derived from multiple indications that would be considered for treatment using BNCT were used. Specifically, the panel consisted of Head and Neck Carcinomas (FaDu and Detroit 562), melanoma (MeWo), non-small cancer lung carcinoma (A549), and breast carcinoma (HCC-1954).

Using standard methods, subcutaneously implanted established mouse xenografts were grown in SCID CB-17 mice. The treatment began when the tumors reached 150-200 mm$^3$ as follows: the BTS or BTS(OMe) arms received 800 mg/kg and the control BPA arm received 200 mg/kg. The animals were euthanized at two (2) hours post-injection. The tumors were harvested, weighed, and digested using the standard methods. The concentration of boron was measured by ICP OES and plotted as microgram per gram tissue. As shown in FIG. 25, the amount of boron in the BTS and BTS(OMe) arms was the highest and consistent with the previous results. However, the absolute uptake varied between the cell lines with the overall lowest uptake observed in the Detroit 562 tumors.

Furthermore, we evaluated whether the observed differences were related to the level of LAT-1 expression. The harvested tumors were stained for LAT-1 by IHC.

As shown in FIG. 26, both FaDu and MeWo tumors had >99% LAT-1 staining (See, 26(A) and 26(B)) while Detroit 562 had 45% staining with some areas of the tumor lacking the LAT-1 expression (See, 26(E)). The stromal cells were also present in the latter specimen. Both HCC-1954 and A549 resulted mid-way between the highest and the lowest degree of staining (See, 26(C) and 26(D)). Based on the foregoing, it is shown that the LAT-1 expression analysis correlated with the boron uptake which confirms that elevated LAT-1 expression is important for superior outcomes of BNCT treatment.

Example 16: Human Clinical Trials for the Treatment of Human Carcinomas Through the Use of BTS & BTS(OMe)

BTS and/or BTS(OMe) are synthesized in accordance with the present invention which specifically accumulate in a tumor cell and are used in the treatment of certain tumors and other immunological disorders and/or other diseases. In connection with each of these indications, two clinical approaches are successfully pursued.

I.) Adjunctive therapy: In adjunctive therapy, patients are treated with BTS and/or BTS(OMe) in combination with a chemotherapeutic or pharmaceutical or biopharmaceutical agent or a combination thereof. Primary cancer targets are treated under standard protocols by the addition of BTS and/or BTS(OMe) and then irradiated. Protocol designs address effectiveness as assessed by the following examples, including but not limited to, reduction in tumor mass of primary or metastatic lesions, increased progression free survival, overall survival, improvement of patients' health, disease stabilization, as well as the ability to reduce usual doses of standard chemotherapy and other biologic agents.

These dosage reductions allow additional and/or prolonged therapy by reducing dose-related toxicity of the chemotherapeutic or biologic agent.

II.) Monotherapy: In connection with the use of the BTS and/or BTS(OMe) in monotherapy of tumors, the BTS and/or BTS(OMe) are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients' health, disease stabilization, as well as the ability to reduce usual doses of standard chemotherapy and other biologic agents.

Dosage

Dosage regimens may be adjusted to provide the optimum desired response. For example, a single BTS and/or BTS (OMe) injection may be administered, several divided doses may be administered over time, or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention is dictated by and directly dependent on (a) the unique characteristics of the BTS and/or BTS(OMe), the individual mechanics of the irradiation mechanism (reactor) and the particular therapeutic or prophylactic effect to be achieved, and (b) the limitations inherent in the art of compounding such a compound for the treatment of sensitivity in individuals.

Clinical Development Plan (CDP)

The CDP follows and develops treatments of cancer(s) and/or immunological disorders using BTS and/or BTS (OMe) of the disclosure which are then irradiated using Neutron Capture Therapy in connection with adjunctive therapy or monotherapy. Trials initially demonstrate safety and thereafter confirm efficacy in repeat doses. Trials are open label comparing standard chemotherapy with standard therapy plus BTS and/or BTS(OMe) which are then irradiated using Boron Neutron Capture Therapy. As will be appreciated, one non-limiting criteria that can be utilized in connection with enrollment of patients is concentration of BTS and/or BTS(OMe) in a tumor as determined by standard detection methods known in the art.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Naturally Occuring Amino Acids.

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE II

Pharmacokinetic Parameters.

| Parameter | BTS | BPA Fructose |
|---|---|---|
| T ½ alpha, min | 2.985 | 1.2883 |
| T ½ beta, min | 70.70 | 180.48 |
| $C_0$ µg/mL | 712.7 | 757.7 |
| CL, mg/(µg/mL)/min | 0.000304 | 0.00011 |
| AUC (0 – t) | 12357.89 | 22484 |
| AUC (0 – ∞) | 13381.9 | 36574.7 |
| $V_{ss}$, mg/µg/mL | 0.0252 | 0.0289 |

The invention claimed is:

1. A method of delivering a borylated amino acid composition to cell for the treatment of disease comprising:
   (i) administering to a patient a Dosage Unit Form comprising a composition having a chemical structure as follows:

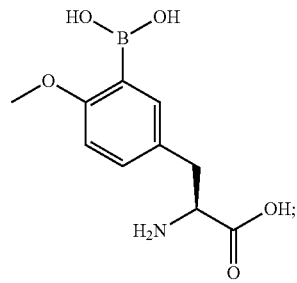 [SMILES: COc1ccc(C[C@H](N)C(=O)O)cc1B(O)O]

(ii) accumulating the Dosage Unit Form into a cell; and
   (iii) irradiating the cell with neutrons.

2. The method of claim 1, wherein the patient is a human.

3. The method of claim 1, wherein the Dosage Unit Form is accumulated into the cell by the LAT-1 amino acid transporter.

4. The method of claim 1, wherein the treatment is Boron Neutron Capture Therapy (BNCT).

5. The method of claim 1, wherein the treatment is Proton Boron Fusion Therapy (PBFT).

6. A kit comprising the Dosage Unit Form of claim 1.
7. The kit of claim 6, further comprising a label.
8. A composition comprising a chemical structure as follows:
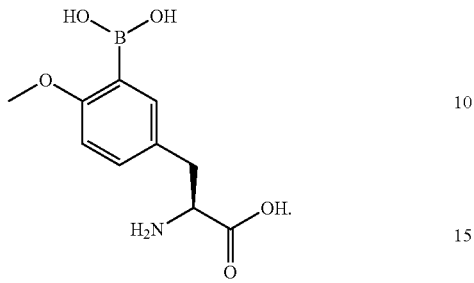
9. A kit comprising the composition of claim 8.
10. A Dosage Unit Form comprising a composition of claim 8.
11. The Dosage Unit Form of claim 10, wherein the Dosage Unit Form is used in Boron Neutron Capture Therapy (BNCT).
\* \* \* \* \*